(12) United States Patent
Lazzari et al.

(10) Patent No.: US 8,399,457 B2
(45) Date of Patent: *Mar. 19, 2013

(54) PHARMACEUTICAL COMPOUNDS

(75) Inventors: Paolo Lazzari, Cagliari (IT); Giovanni Loriga, Sassari (IT); Stefania Ruiu, Cagliari (IT); Ilaria Manca, Sassari (IT); Luca Pani, Cagliari (IT); Gerard Aime Pinna, Sassari (IT)

(73) Assignee: Neuroscienze Pharmaness S.C. A.R.L., Pula Cagliari (IT)

( * ) Notice: Subject to any disclaimer, the term of this patent is extended or adjusted under 35 U.S.C. 154(b) by 528 days.

This patent is subject to a terminal disclaimer.

(21) Appl. No.: 12/512,818

(22) Filed: Jul. 30, 2009

(65) Prior Publication Data

US 2010/0028257 A1   Feb. 4, 2010

(30) Foreign Application Priority Data

Jul. 31, 2008 (IT) .............................. MI2008A1426

(51) Int. Cl.
*A61P 21/02* (2006.01)
*A61K 31/551* (2006.01)
*C07D 487/08* (2006.01)

(52) U.S. Cl. ........................................ 514/221; 540/556
(58) Field of Classification Search .................. 514/221; 540/556
See application file for complete search history.

(56) References Cited

U.S. PATENT DOCUMENTS

| 5,672,601 | A | 9/1997 | Cignarella |
| 6,028,084 | A | 2/2000 | Barth et al. |
| 2003/0003145 | A1 | 1/2003 | Abramovici et al. |
| 2003/0195217 | A1 | 10/2003 | Cignarella et al. |
| 2003/0196217 | A1 | 10/2003 | Mukerji et al. |
| 2005/0203123 | A1 | 9/2005 | Dolle et al. |
| 2007/0027328 | A1* | 2/2007 | Aronhime et al. ............ 548/537 |

FOREIGN PATENT DOCUMENTS

| WO | WO 01/46198 A2 | 6/2001 |
| WO | WO 02/42309 A1 | 5/2002 |
| WO | WO 2004/011468 A1 | 2/2004 |
| WO | WO 2004/060321 A2 | 7/2004 |
| WO | WO 2004/089372 A1 | 10/2004 |
| WO | WO 2004/100468 A1 | 11/2004 |
| WO | WO 2005/066164 A1 | 7/2005 |
| WO | WO 2005/092836 A1 | 10/2005 |
| WO | WO 2005/108402 A1 | 11/2005 |
| WO | WO 2006/113468 A2 | 10/2006 |

OTHER PUBLICATIONS

Trescot et al., Opioid Pharmacology, Pain Physician, vol. 11, pp. S133-S153, 2008.*
Gérard A. Pinna et al., "N-3(9)-Arylpropenyl-N-9(3)-propionyl-3,9-diazabicyclo[3.3.1]nonanes as μ-Opioid Receptor Agonists. Effects on μ-Affinity of Arylalkenyl Chain Modifications" 2002, pp. 1929-1937, vol. 10, Bioorganic & Medicinal Chemistry.
Anastassia Hatzoglou et al., "The antiproliferative effect of opioid receptor agonists on the T47D human breast cancer cell line, is partially mediated through opioid receptors" 1996, pp. 199-207, vol. 296, European Journal of Pharmacology.
Deborah D. Stephan et al., "Changes in intraocular pressure and pupil size following intramuscular administration of hydromorphone hydrochloride and acepromazine in clinically normal dogs" 2003, pp. 73-76, vol. 6, Veterinary Ophthalmology.
Juanita Dortch-Carnes et al., "Morphine-Stimulated Nitric Oxide Release in Rabbit Aqueous Humor" Jan. 2007, pp. 185-190, vol. 84, *Exp Eye Res*.
R. Alexander et al., "Remifentanil prevents an increase in intraocular pressure after succinylcholine and tracheal intubation" 1998, pp. 606-607, vol. 81, British Journal of Anaesthesia.
M.J. Glass et al., "Opioids and food intake: distributed functional neural pathways" 1999, pp. 360-368, vol. 33, No. 5, Neuropeptides.
Cathy E. McNamee et al., "Physicochemical Characterization of PEG1500-12-acyloxy-stearate Micelles and Liquid Crystalline Phases" 2005, pp. 8146-8154, vol. 21, Langmuir.
Rajib K. Mitra et al., "Physicochemical investigations of microemulsification of eucalyptus oil and water using mixed surfactants (AOT + Brij-35) and butanol" 2005, pp. 565-577, vol. 283, Journal of Colloid and Interface Science.
Mack Publishing Company, "The Science and Pharmacy" 1995, pp. 1457, vol. II, Remington: The Science and Practice of Pharmacy.
E. Gracia-Garcia et al., "Colloidal carriers and blood-brain barrier (BBB) translocation: A way to deliver drugs to the brain?" 2005, 274-292, vol. 298, International Journal of Pharmaceutics.
Jörg Kreuter, "Nanoparticulate systems for brain delivery of drugs" 2001, pp. 65-81, vol. 47, Advance Drug Delivery Reviews.
Maria Teresa Peracchia et al., Synthesis of a Novel Poly(MePEG cyanoacrylate-*co*-alkyl cyanoacrylate) Amphiphilic Copolymer for Nanoparticle Technology, 1997, pp. 846-851, vol. 30, Macromolecules.

(Continued)

*Primary Examiner* — Brenda Coleman
(74) *Attorney, Agent, or Firm* — Arent Fox LLP

(57) ABSTRACT

Nonane and decane diazabicyclic derivatives having homopiperazine as main ring, having affinity for the opioidergic μ and/or δ and/or k receptors and/or for all their receptorial subclasses, with central and/or peripheral activity, having formula (I), the isomeric forms and their mixtures included, wherein one or more atoms are in the corresponding isotopic forms:

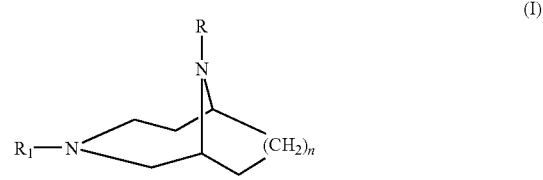

wherein:
n is an integer equal to 1 or 2;
one of the substituents R and $R_1$ of the nitrogen atoms of the diazabicyclic ring is a —C(O)—$R_B$ group, wherein $R_B$ is a $C_1$-$C_{10}$ alkyl group, linear or branched when possible,
the other remained substituent of R and $R_1$ has the meanings reported in the description.

35 Claims, No Drawings

OTHER PUBLICATIONS

Luca Costantino et al., "Peptide-derivatized biodegradable nanoparticles able to cross the blood-brain barrier" 2005, pp. 84-96, vol. 108, Journal of Controlled Release.

Barbara Stella et al., "Design of Folic Acid-Conjugated Nanoparticles for Drug Targeting" Nov. 2000, pp. 1452-1464, vol. 89, No. 11, Journal of Pharmaceuticals Sciences.

Stefania Ruiu et al., "Synthesis and Characterization of NESS 0327: A Novel Putative Antagonist of the $CB_1$ Cannabinoid Receptor" 2003, pp. 363-370, vol. 306, No. 1, The Journal of Pharmacology and Experimental Therapeutics.

* cited by examiner

PHARMACEUTICAL COMPOUNDS

The present invention relates to pharmaceutical compositions comprising diazabicyclic active principles having affinity for the opioidergic receptors μ and/or δ and/or k and/or for the receptorial subclasses thereof, the corresponding solvates and pharmaceutically acceptable salts.

More specifically the present invention relates to pharmaceutical compositions wherein the diazabicyclic active principles are diazabicyclic nonane and decane compounds having a homopiperazine main ring and having high affinity and selectivity for one or more opioidergic receptors μ, δ, k or the receptorial subclasses thereof. The compounds of the present invention can substantially act either only on one receptor of this receptorial class or simultaneously on more opioid receptors.

Diazabicyclic compounds having affinity for opioidergic receptors are known in the prior art. In US patent application 2003/0195,217 3,9-diazabicyclo[3.3.1]nonane compounds having central analgesic activity mediated by the opioidergic receptors, are described. The analgesic activity is comparable to that induced by morphine, but with lower side effects. The study of these diazabicyclic compounds has also been treated in the publication in *Bioorganic & Medicinal Chemistry*, 10 (2002) 19, 29-1937 wherein it is pointed out the effect of various substituents of the bicyclic structure on the affinity towards the opioidergic receptors μ, δ and k. Another class of diazabicyclic compounds having affinity towards the opioidergc receptors μ, δ and k, and the corresponding pharmaceutical forms, is described in patent application WO 2004/011,468. In particular, said class of compounds is formed of diazabicyclo nonanes and decanes of general formula

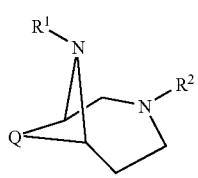

(A)

wherein Q is —CH$_2$—CH$_2$— or —CH$_2$—CH$_2$—CH$_2$— and one between R$^1$ and R$^2$ is —CH$_2$—CH$_2$—CH$_2$—R$^3$ or —CH$_2$—CH=CH—R$^3$ or —CH$_2$—C≡C—R$^3$ wherein R$^3$ is aryl or heteroaryl and the other between R$^1$ and R$^2$ is —C(O)R$^4$ wherein R$^4$ is alkyl, or cycloalkyl, or cycloalkylalkyl, or aryl or arylalkyl.

U.S. Pat. No. 5,672,601 describes 3,8-diaza-bicylo[32.1]-octane compounds, and the corresponding pharmaceutical forms, having central analgesic activity mediated by the opioidergic receptors μ.

Patent application WO 2005/108,402 relates to 3,6-diazabicyclo[3.1.1]heptane derivatives having central analgesic activity selectively mediated by the receptors μ.

The above mentioned patents and patent applications describe the use of the diazabicyclic compounds having affinity for the opioidergic receptors for the pain treatment.

In the above mentioned patent application WO 2004/011,468 it is stated that the opioidergic compounds, besides the use for the treatment of different kinds of pain (post-surgery pain, chronic pain such as neuropathic pain), can be used for the therapeutical treatment of other diseases and disorders such as allergic dermatitis, sexual disfunctions, alcoholism, nausea, vomit, depression, tabagism, obesity and disorders associated to the food intake, use of abuse substances (for ex. heroin, cocaine), spinal lesion, cerebral trauma, shock, stroke, gastrointestinal disorders. Eur. J. Pharmacol. 296 (1996) 199-207 reports the antiproliferative activity of agonist compounds of opioidergic receptors on a human cellular line of breast tumour. The article therefore discloses the antitumoural activity of said agonist compounds. In the articles Veterinary Opthamology (2003) 6, 1, 73-76; Exp. Eye Res. 2007 January 84(1) 185-190; British Journal of Anaesthesia 1998, 81 606-607 it is pointed out the capability of agonist compounds of the opioidergic receptors of reducing the intraocular pressure and consequently the use of said compounds for eye diseases, such as glaucoma. In the article published in Neuropeptides (1999) 33(5) 360-368 it is reported the effect of compounds modulating the opioidergic receptors on the food intake, in particular it is stated that agonists and antagonists of the opioidergic receptors can, respectively, increase and decrease the food intake.

Patent application WO 06/113,468 describes the use of compounds modulating the opioidergic receptors for the treatment of arthritis, psoriasis, asthma, cardiac disorders, sexual disfunctions, pain, incontinence and disorders of the urogenital tract.

Patent application US 2005/0203,123 relates to compounds antagonist of the opioidergic receptors and their use for the treatment of gastrointestinal disorders, pain, obesity, Alzheimer and Parkinson diseases. The use of opioidergic compounds for the treatment of diabetes and atherosclerosis is described in patent applications WO 05/092,836 and WO 05/066,164.

Patent application WO 04/089,372 describes the use of compounds capable of modulating the opioidergic receptors for the treatment or prevention of central nervous system disorders, such as anxiety and depression.

Patent application WO 04/060,321 relates to therapeutic compositions comprising agonists of the opioidergic receptors with cardioprotective effects.

Patent applications WO 02/42,309, WO 01/46,198 describe the use of opioidergic compounds as immunostimulants or immunosuppressants.

The need was felt have available pharmaceutical forms comprising new diazabicyclic compounds effective in the treatment of the above mentioned pathologies, having a better tolerance with respect to morphine in the pain treatment able to guarantee high bioavailability of the active principles in the treatment of the mentioned pathologies.

Pharmaceutical compositions solving the above described technical problem have been surprisingly and unexpertedly found by the Applicant.

It is an object of the present invention diazabicyclic nonane and decane derivatives with homopiperazine main ring, having affinity for the opioidergic receptors μ and/or δ and/or k and/or for their receptorial subclasses, having central and/or peripheral activity, of formula (I), comprising the isomeric forms and the mixtures thereof, wherein the ring atoms can be optionally in different isotopic forms:

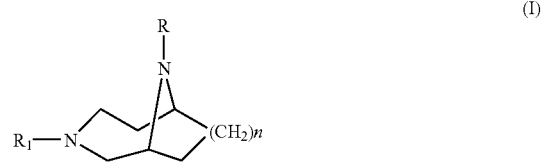

(I)

wherein:
n is an integer equal to 1 or 2,
one of the substituents R and $R_1$ of the nitrogen atoms of the diazabicyclic ring is a —C(O)—$R_B$ group, wherein $R_B$ is a $C_1$-$C_{10}$ alkyl group, linear or branched when possible,
the other substituent between R and $R_1$ is selected from the following groups from (II) to (X):
structure (II)

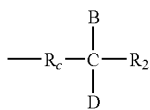
(II)

wherein:
$R_c$ is a bivalent saturated $C_3$-$C_{10}$ aliphatic chain, linear or branched when possible,
B is a group selected from hydrogen, isothiocyanate, CN, OR', C(O)OR', C(O)R', C(O)NR'R", NR'R", R' and R", equal to or different from each other, being selected from hydrogen, linear or branched when possible, $C_1$-$C_7$ alkyl, $C_1$-$C_7$ alkoxy, $C_1$-$C_7$ alkylthio, $C_1$-$C_7$ haloalkyl, $C_1$-$C_7$ haloalkoxy, $C_3$-$C_{15}$ cycloalkyl, aryl or heteroaryl,
D and $R_2$, equal to or different from each other, are substituents selected from:
hydrogen, with the proviso that in formula (II) at least one substituent among B, D and $R_2$ is different from hydrogen,
$C_1$-$C_{10}$ alkyl, linear or branched when possible,
aryl or heteroaryl
$C_3$-$C_{15}$ cycloalkyl,
formula (III):

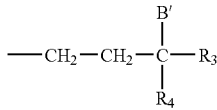
(III)

wherein:
B' is equal to B as defined above,
$R_3$ is hydrogen; or, respectively, an alkyl, aryl, heteroaryl or cycloalkyl substituent as defined for $R_2$,
$R_4$ has the following meanings:
$C_1$-$C_{10}$ alkyl, linear or branched when possible,
$C_3$-$C_{15}$ cycloalkyl, optionally containing one or more heteroatoms, preferably selected from O, S, N,
when B' and $R_3$ are not both hydrogen, $R_4$ has the further meanings of aryl or heteroaryl,
formula (IV):

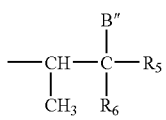
(IV)

wherein:
B" as the same meaning of B' as defined above,
$R_5$ has the same meaning of $R_3$ as defined above,
$R_6$ has the same meaning of $R_4$ as defined above, or is an aryl or heteroaryl,
formula (V):

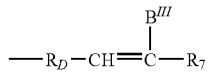
(V)

wherein:
$R_D$ is a bivalent saturated or unsaturated $C_2$-$C_8$ aliphatic chain, linear or branched when possible,
$B^{III}$ and $R_7$, equal to or different from each other, have the same meaning of $R_2$ as defined above, with the proviso that $B^{III}$ and $R_7$ are not both hydrogen,
formula (VI):

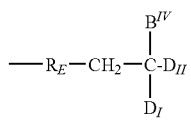
(VI)

wherein:
$R_E$ is an unsaturated bivalent $C_2$-$C_8$ aliphatic chain, linear or branched when possible,
$B^{IV}$ has the same meaning of B as defined above,
$D_I$ and $D_{II}$ have the same meaning of $R_2$ as defined above, with the proviso that in formula (VI) at least one substituent among $B^{IV}$, $D_{II}$ and $D_I$ is different from hydrogen,
formula (VII):

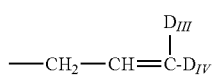
(VII)

wherein:
$D_{III}$ and $D_{IV}$, equal to or different from each other, have the same meaning of $R_2$, as defined above, but excluding hydrogen, formula (VIII):

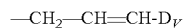
—$CH_2$—CH═CH-$D_V$           (VIII)

wherein $D_V$ has the meanings of $R_4$ as defined above but excluding aryl or heteroaryl, formula (IX):

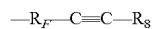
—$R_F$—C≡C—$R_8$           (IX)

wherein $R_F$ is a saturated or unsaturated bivalent $C_2$-$C_8$ aliphatic chain, linear or branched when possible and $R_8$ has the same meaning as $R_2$ as defined above, but excluding the meaning of $R_8$ equal to hydrogen, formula (X):

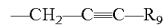
—$CH_2$—C≡C—$R_9$           (X)

wherein $R_9$ has the meanings of $R_4$ as defined above but excluding aryl or heteroaryl.
When the substituent B in formula (II) is a group selected from OR', C(O)OR', C(O)R', C(O)NR'R", NR'R" and R' and/ or R" have the meaning of $C_3$-$C_{15}$ cycloalkyl, said cycloalkyl can optionally contain one or more heteroatoms, preferably selected from O, S, N.

When the substituent B in formula (II) is a group selected from OR', C(O)OR', C(O)R', C(O)NR'R" NR'R" and R' and/or R" have the meaning of $C_3$-$C_{15}$ cycloalkyl, aryl and heteroaryl, said $C_3$-$C_{15}$ cycloalkyl, aryl and heteroaryl can optionally be substituted with one or more groups selected from hydroxy, halogen, linear or branched when possible $C_1$-$C_{10}$ alkyl.

When D and/or $R_2$ in formula (II) have the meaning of linear or branched when possible $C_1$-$C_{10}$ alkyl, the alkyl can optionally be substituted with one or more groups, equal to or different from each other, selected from hydroxy, halogen, CN, $C_3$-$C_{15}$ cycloalkyl, aryl, heteroaryl. Said cycloalkyl can optionally contain one or more heteroatoms, preferably selected from O, S, N. Said $C_3$-$C_{15}$ cycloalkyl, aryl and heteroaryl can optionally be substituted with one or more groups selected from hydroxy, halogen, linear or branched when possible $C_1$-$C_{10}$ alkyl, $C_1$-$C_7$ alkoxy, $C_1$-$C_7$ alkylthio, $C_1$-$C_7$ haloalkyl, $C_1$-$C_7$ haloalkoxy.

When D and/or $R_2$ in formula (II) and/or $R_6$ in formula (IV) have the meaning of aryl or heteroaryl, these structures can optionally be substituted with one or more of the following groups, equal to or different from each other, selected from: linear or branched when possible $C_1$-$C_{10}$ alkyl, optionally substituted with one or more groups, equal to or different from each other, selected from hydroxy, halogen, CN, $C_3$-$C_{15}$ cycloalkyl, optionally containing one or more heteroatoms, preferably selected from O, S, N. Said cycloalkyl can optionally be substituted with one or more groups, equal to or different from each other, selected from hydroxy, halogen, linear or branched when possible $C_1$-$C_{10}$ alkyl, $C_1$-$C_7$ alkoxy, $C_1$-$C_7$ alkylthio, $C_1$-$C_7$ haloalkyl, $C_1$-$C_7$ haloalkoxy, arylalkyl or aryl or heteroaryl or heteroarylalkyl, these groups are optionally substituted with one or more groups, equal to or different from each other, selected from hydroxy, halogen, linear or branched when possible $C_1$-$C_{10}$ alkyl, $C_1$-$C_7$ alkoxy, $C_1$-$C_7$ alkylthio, $C_1$-$C_7$ haloalkyl, $C_1$-$C_7$ haloalkoxy.

When D and/or $R_2$ in formula (II) have the meaning of $C_3$-$C_{15}$ cycloalkyl, said cycloalkyl optionally contains one or more heteroatoms, preferably selected from O, S, N. Furthermore cycloalkyl can optionally be substituted with one or more of the following groups, equal to or different from each other, selected from: $C_1$-$C_{10}$ alkyl, linear or branched when possible, optionally substituted with one or more groups, equal to or different from each other, selected from hydroxy, halogen, CN, $C_3$-$C_{15}$ cycloalkyl, optionally containing one or more heteroatoms, preferably selected from O, S, N. Said cycloalkyl can optionally be substituted with one or more groups, equal to or different from each other, selected from hydroxy, halogen, linear and branched when possible $C_1$-$C_{10}$ alkyl, $C_1$-$C_7$ alkoxy, $C_1$-$C_7$ alkylthio, $C_1$-$C_7$ haloalkyl, $C_1$-$C_7$ haloalkoxy, arylalkyl or aryl or heteroaryl or heteroarylalkyl, said groups optionally substituted with one or more groups, equal to or different from each other, selected from hydroxy, halogen, linear or branched when possible $C_1$-$C_{10}$ alkyl, $C_1$-$C_7$ alkoxy, $C_1$-$C_7$ alkylthio, $C_1$-$C_7$ haloalkyl, $C_1$-$C_7$ haloalkoxy.

In formula (III) when $R_4$ has the meaning of $C_1$-$C_{10}$ alkyl, linear or branched when possible, said $C_1$-$C_{10}$ alkyl can optionally be substituted with one or more groups equal to or different from each other selected from hydroxy, halogen, CN, aryl, heteroaryl or $C_3$-$C_{10}$ cycloalkyl, optionally containing one or more heteroatoms, preferably selected from O, S, N. Said $C_3$-$C_{15}$ cycloalkyl, aryl or heteroaryl can optionally be substituted with one or more groups equal to or different from each other selected from hydroxy, halogen, linear or branched when possible $C_1$-$C_{10}$ alkyl, arylalkyl or aryl or heteroaryl or heteroarylalkyl. Said arylalkyl or aryl or heteroaryl or heteroarylalkyl can optionally be substituted with one or more groups, equal to or different from each other, selected from hydroxy, halogen, linear or branched when possible $C_1$-$C_{10}$ alkyl, $C_1$-$C_7$ alkoxy, $C_1$-$C_7$ alkylthio, $C_1$-$C_7$ haloalkyl, $C_1$-$C_7$ haloalkoxy.

In formula (III) when $R_4$ has the meaning of $C_3$-$C_{15}$ cycloalkyl, optionally containing one or more heteroatoms, preferably selected from O, S, N, said cycloalkyl can optionally be substituted with one or more of the following groups, equal to or different from each other:
linear or branched when possible $C_1$-$C_{10}$ alkyl, optionally substituted with one or more groups, equal to or different from each other, selected from the following: hydroxy, halogen, CN,
$C_3$-$C_{15}$ cycloalkyl, optionally containing one or more heteroatoms, equal to or different from each other, preferably selected from O, S, N, said cycloalkyl optionally substituted with one or more groups, equal to or different from each other: hydroxy, halogen, $C_1$-$C_{10}$ alkyl, linear or branched when possible, arylalkyl or aryl or heteroaryl or heteroarylalkyl. Said arylalkyl or aryl or heteroaryl or heteroarylalkyl can optionally be substituted with one or more groups, equal to or different from each other, selected from: hydroxy, halogen, linear and branched when possible $C_1$-$C_{10}$ alkyl, $C_1$-$C_7$ alkoxy, $C_1$-$C_7$ alkylthio, $C_1$-$C_7$ haloalkyl, $C_1$-$C_7$ haloalkoxy, arylalkyl or aryl or heteroaryl or heteroarylalkyl, optionally substituted with one or more groups, equal to or different from each other, selected from hydroxy, halogen, linear or branched when possible $C_1$-$C_{10}$ alkyl, $C_1$-$C_7$ alkoxy, $C_1$-$C_7$ alkylthio, $C_1$-$C_7$ haloalkyl, $C_1$-$C_7$ haloalkoxy.

In formula (III) when B' and $R_3$ are not both hydrogen and $R_4$ can also have the meaning of aryl or heteroaryl, each of aryl and heteroaryl can optionally be substituted with one or more of the following groups, equal to or different from each other:
linear or branched when possible $C_1$-$C_{10}$ alkyl, optionally substituted with one or more groups, equal to or different from each other, selected from the following: hydroxy, halogen, CN,
$C_3$-$C_{15}$ cycloalkyl, optionally containing one or more heteroatoms, equal to or different from each other, preferably selected from O, S, N. Said cycloalkyl can optionally be substituted with one or more of the following groups, equal to or different from each other: hydroxy, halogen, linear or branched when possible $C_1$-$C_{10}$ alkyl, arylalkyl or aryl or heteroaryl or heteroarylalkyl. Said arylalkyl or aryl or heteroaryl or heteroarylalkyl can optionally be substituted with one or more groups, equal to or different from each other, selected from hydroxy, halogen, linear and branched when possible $C_1$-$C_{10}$ alkyl, $C_1$-$C_7$ alkoxy, $C_1$-$C_7$ alkylthio, $C_1$-$C_7$ haloalkyl, $C_1$-$C_7$ haloalkoxy,
arylalkyl or aryl or heteroaryl or heteroarylalkyl, optionally substituted with one or more groups, equal to or different from each other, selected from hydroxy, halogen, linear or branched when possible $C_1$-$C_{10}$ alkyl, $C_1$-$C_7$ alkoxy, $C_1$-$C_7$ alkylthio, $C_1$-$C_7$ haloalkyl, $C_1$-$C_7$ haloalkoxy.

Where not otherwise specified, the following meanings are meant in the present invention.

By alkyl it is meant a saturated $C_1$-$C_{40}$, preferably $C_1$-$C_{10}$, aliphatic chain, linear or branched when possible, the aliphatic chain having a free valence.

By bivalent saturated aliphatic chain it is meant a linear or branched when possible hydrocarbon chain, formed of carbon atoms saturated with hydrogen atoms, and linked to each other by single bonds, having at each end of the backbone a free valence.

By bivalent unsaturated aliphatic chain it is meant a hydrocarbon chain formed of carbon atoms linked to each other by single bonds and by at least a double or triple bond, the chain having at each end a free valence, the other valences of the carbon atoms are saturated by hydrogen atoms.

By cycloalkyl it is meant a cycloalkyl with a ring, for example from 3 to 8 carbon atoms, preferably from 5 to 6 carbon atoms, or a structure having more condensed cycloalkyl rings, preferably with 8-19 carbon atoms.

By saturated heterocycle it is meant a cycloalkyl as defined above wherein at least one carbon atom of a cycloalkyl ring is substituted by an heteroatom preferably selected from S, O, N.

By unsaturated heterocycle it is meant a saturated heterocycle as defined above but with one or more double bonds in one or more cycloalkyl rings, with the proviso that the ring structure is not aromatic.

By halogen, an atom selected from fluorine, chlorine, bromine, iodine is meant.

By haloalkyl it is meant an alkyl wherein one or more hydrogen atoms are substituted with halogen atoms, for example trifluoromethyl, 1-bromo-n-butyl, pentachloroethyl.

By aryl it is meant a $C_6$ aromatic monocyclic radical or a $C_7$-$C_{19}$ polycyclic radical wherein at least one ring is aromatic, said radicals containing carbon and hydrogen atoms.

By alkylaryl it is meant a $C_1$-$C_7$ alkyl group, linear or branched when possible, wherein one hydrogen atom is substituted with an aryl group as defined above, wherein the free valence is on the aryl.

By arylalkyl it is meant a $C_1$-$C_{10}$ alkyl linear or branched when possible, linked to an aryl as defined above, wherein the free valence is in the alkyl moiety, for example benzyl can be mentioned.

By heteroaryl it is meant an aryl as defined above, but even with 5 atom rings, wherein at least one atom of the ring is an heteroatom preferably selected from S, O, N.

By alkylheteroaryl it is meant a $C_1$-$C_7$ alkyl group, linear or branched when possible, wherein one hydrogen atom is substituted with an heteroaryl group as defined above.

By heteroarylalkyl it is meant an arylalkyl as defined above wherein at least one atom of the ring is an heteroatom preferably selected from S, O, N, but even with 5 atom rings.

By compound having affinity towards the receptors it is meant a compound having in vivo and/or in vitro agonist activity, or antagonist, or partial agonist, or partial antagonist, or inverse agonist, or inverse antagonist, or inverse partial agonist, or inverse partial antagonist activity towards the receptors. The meaning of said terms is known to the skilled in the field.

By opioid receptors and opioidergic receptors are meant the receptors µ and/or δ and/or k and/or their receptorial subclasses.

By receptorial subclasses of the opioidergic receptors µ, δ and k, the receptors µ1, µ2, δ2, k1, k2 and k3 are meant.

The preferred compounds of formula (I) are those wherein one of the substituents R and $R_1$ of the nitrogen atoms of the diazabicyclic ring is a group —C(O)—$R_B$, the other substituent remained between R and $R_1$ is selected from the structures of formula (II) to (X) wherein:
in formula (II) $R_c$ is a bivalent saturated $C_3$-$C_7$ aliphatic chain, linear or branched when possible, B is hydrogen,
in formula (III) B' is hydrogen, $R_3$ is a substituent selected from alkyl, aryl, heteroaryl or cycloalkyl as defined in $R_2$, wherein $R_4$ is as above defined, further comprising the meaning of aryl or heteroaryl as defined above,
in formula (IV) B" is hydrogen,
in formula (V) $R_D$ is a saturated or unsaturated bivalent $C_2$-$C_7$ aliphatic chain, linear or branched when possible, $B^{III}$ and $R_7$, equal to or different from each other, have the same meaning of $R_2$ with the proviso that $B^{III}$ and $R_7$ are not both hydrogen,
in formula (VI) $R_E$ is a bivalent unsaturated $C_2$-$C_5$ aliphatic chain, linear or branched when possible, $B^{IV}$ is hydrogen, $D_{II}$ and $D_I$ have the same meaning of $R_2$, with the proviso that in formula (VI) at least one substituent between $D_{II}$ and $D_I$ is different from hydrogen,
formulae (VII) to (X) are as defined above.

The most preferred compounds of formula (I) are those wherein one of the substituents R and $R_1$ is a group —C(O)—$R_B$, wherein $R_B$ is a $C_1$-$C_4$ alkyl group linear or branched when possible, the other substituent remained between R and $R_1$ is selected from the structures of formulae (II) to (X) wherein:
in formula (II) $R_c$ is a bivalent saturated $C_3$-$C_7$ aliphatic chain, linear or branched when possible, B is hydrogen,
in formula (III) B' is hydrogen, $R_3$ is a substituent selected from alkyl, aryl, heteroaryl or cycloalkyl as defined for $R_2$, wherein $R_4$ comprises also the meaning of aryl or heteroaryl, $R_3$ being different from hydrogen and B being equal to hydrogen,
in formula (IV) B" is hydrogen,
in formula (V) $R_D$ is a bivalent saturated or unsaturated $C_2$-$C_5$ aliphatic chain, linear or branched when possible, $B^{III}$ and $R_7$, equal to or different from each other, have the same meaning of $R_2$, with the proviso that $B^{III}$ and $R_7$ are not both hydrogen,
in formula (VI) $R_E$ is an unsaturated bivalent $C_2$-$C_5$ aliphatic chain, linear or branched when possible, $B^{IV}$ is hydrogen, $D_{II}$ and $D_I$ have the same meaning of $R_2$, with the proviso that in formula (VI) at least one substituent between $D_{II}$ and $D_I$ is different from hydrogen,
formulae (VII) to (X) are as defined above.

The still more preferred compounds of formula (I) are those wherein:
one of the substituents R and $R_1$ is a group —C(O)—$R_B$, wherein $R_B$ is methyl or ethyl, the other substituent remained between R and $R_1$ is selected from the structures of formula (II) to (X) wherein:
In formula (II) $R_c$ is a bivalent saturated $C_3$ alkyl chain, linear or branched when possible, B is hydrogen,
in formula (III) B' is hydrogen, $R_3$ is a substituent selected from alkyl, aryl, heteroaryl or cycloalkyl as defined in $R_2$, wherein $R_4$ comprises also the meaning of aryl or heteroaryl, $R_3$ being different from hydrogen and B being equal to hydrogen,
in formula (IV) B" is hydrogen,
in formula (V) $R_D$ is a bivalent saturated or unsaturated $C_2$-$C_5$ aliphatic chain, linear or branched when possible, $B^{III}$ and $R_7$, equal to or different from each other, have the same meaning of $R_2$, with the proviso that $B^{III}$ and $R_7$ are not both hydrogen,
in formula (VI) $R_E$ is an unsaturated bivalent $C_3$ aliphatic chain, linear or branched when possible, $B^{IV}$ is hydrogen, $D_{II}$ and $D_I$ have the same meaning of $R_2$, with the proviso that in formula (VI) at least one substituent between $D_{II}$ and $D_I$ is different from hydrogen,
formulae (VII) to (X) are as defined above.

In particular the most preferred compounds are those of formula (I) wherein:
one of the substituents R and $R_1$ is a group —C(O)—$R_B$, wherein $R_B$ is methyl or ethyl, the other substituent remained between R and $R_1$ is selected from the following formulae:

formula (III) wherein B' is hydrogen, R₃ is a substituent selected from alkyl, aryl, heteroaryl or cycloalkyl as defined in R₂, wherein R₄ comprises also the meaning of aryl or heteroaryl:

formula (VIII) wherein $D_{III}$ and $D_{IV}$ equal to or different from each other, have the meaning of R₂ but excluding hydrogen, formula (VIII) wherein $D_V$ has the meaning of R₄ but excluding aryl or heteroaryl, formula (X) wherein R₉ has the meanings of R₄ but excluding aryl or heteroaryl.

The specific compounds of formula (I) are the following:

(XX)
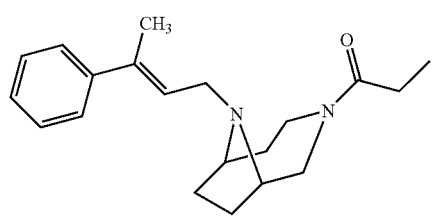

(XXI)
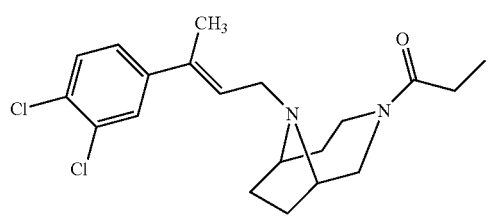

(XXII)
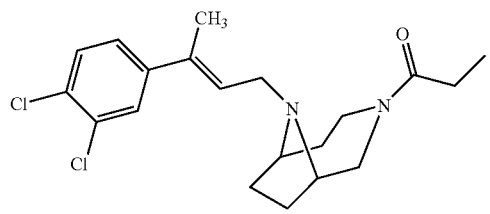

(XXIII)
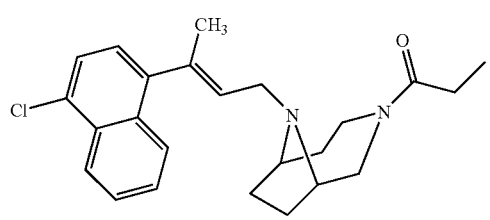

(XXIV)
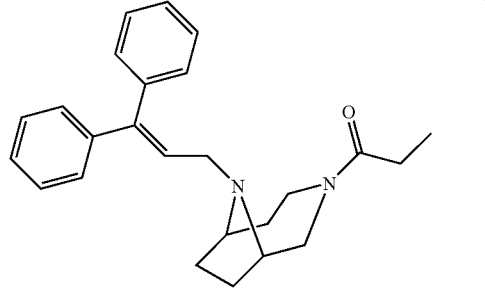

(XXV)
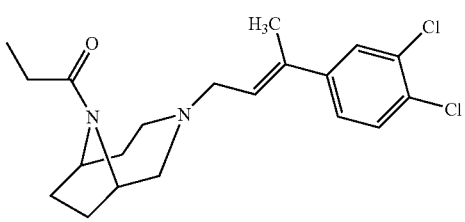

(XXVI)
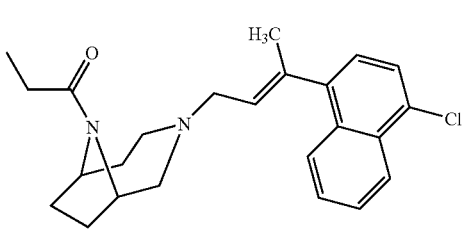

(XXVII)
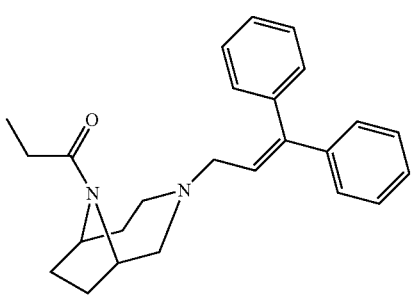

(XXVIII)
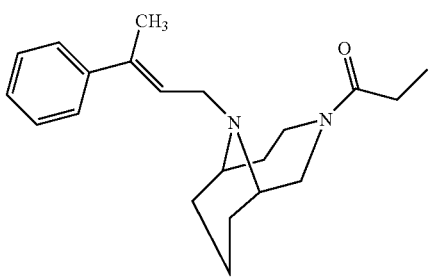

(XXIX)
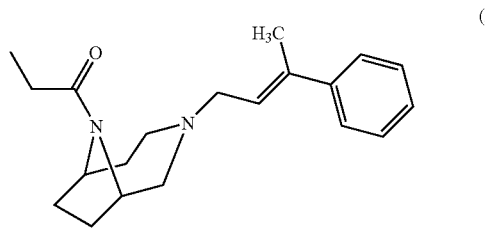

(XXX)
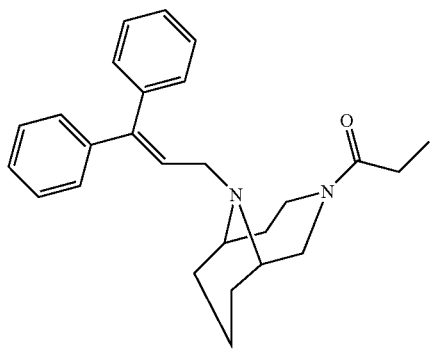
(XXXI)
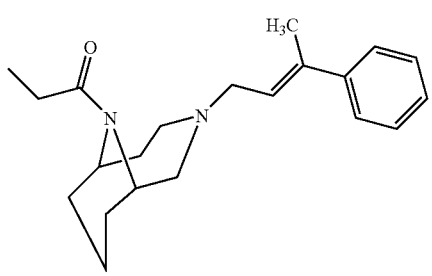
(XXXII)
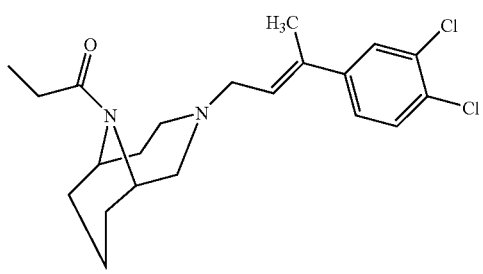
(XXXIII)
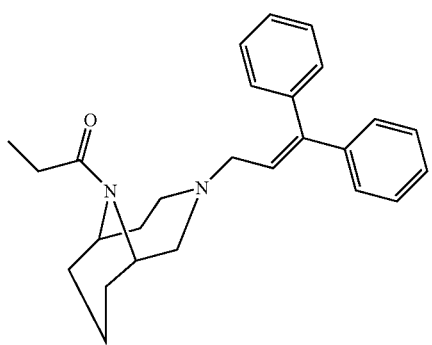
(XXXIV)
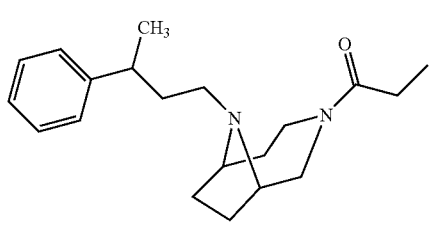
(XXXV)
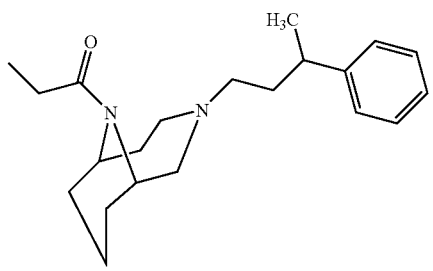
(XXXVI)
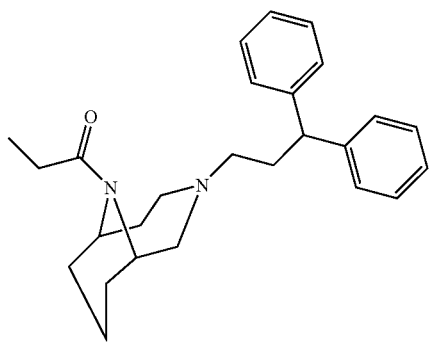
(XXXVII)
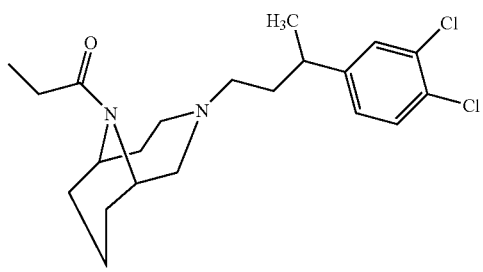
(XXXVIII)
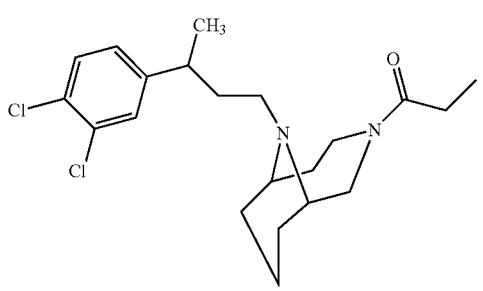
(XXXIX)
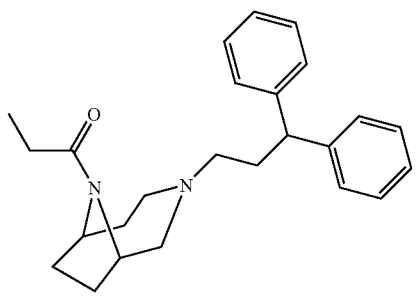

(XXXX)
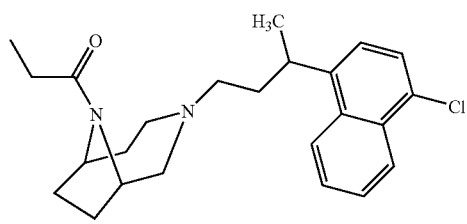

(XXXXV)
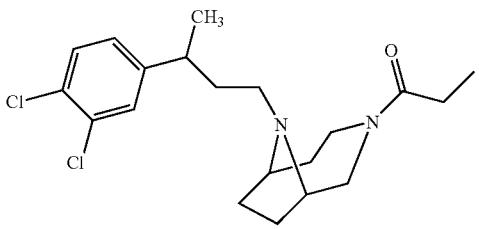

(XXXXI)
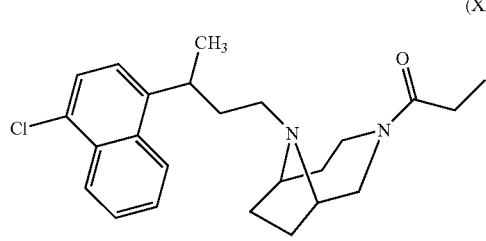

(XXXXVI)
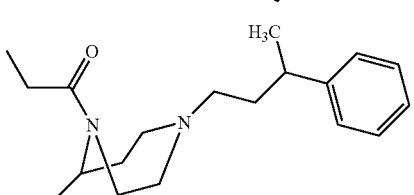

(XXXXII)
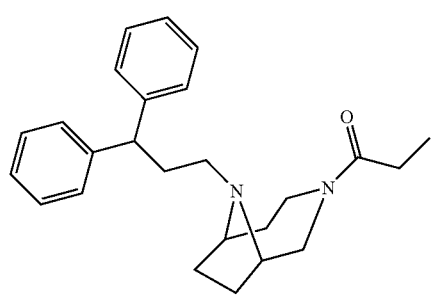

(XXXXVII)
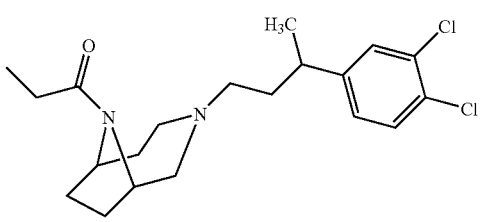

(XXXXIII)

(XXXXIV)

As said, the hydrates, solvates and the pharmaceutically acceptable salts of the compounds of formula (I), including the various isomers (cis and trans isomers, optical isomers when one or more chiral centres are present in the compounds) and corresponding mixtures of the compounds of formula (I), are a further object of the present invention. The meaning of the hydrate and solvate terms is well known to the skilled in the field. In particular by hydrate it is meant the compound containing one or more molecules of hydration water, generally from 1 to 10 molecules of water. By solvate it is meant that the compound contains one or more molecules of solvent different from water, preferably from 1 to 10 molecules of water.

By pharmaceutically acceptable salts are meant all the salts obtained by treating the compounds of formula (I) with organic or inorganic acids acceptable from the pharmaceutical point of view. For example hydrochlorides, sulphates, fumarates, oxalates, citrates, hydrogensulphates, succinates, paratoluensulphonates can be mentioned. See the volume: "Remington, The Science and Practice of Pharmacy", vol. II 1995, page 1457.

The metabolites derived from the administration in an individual and in an animal of the compounds of formula (I) are a further object of the present invention.

It has been surprisingly and unexpectedly found by the Applicant that the compounds of formula (I) of the invention have both in vitro and/or in vivo one or more of the following activities towards the opioidergic receptors μ and/or δ and/or k and/or the receptorial subclasses thereof, such as the receptors $\mu_1$, $\mu_2$ and $\mu_3$: agonist, or antagonist, or partial agonist, or partial antagonist, or inverse agonist, or inverse antagonist, or inverse partial agonist, or inverse partial antagonist. In particular, when the compounds of formula (I) show agonist activity towards one or more receptors of the opioidergic system, they can be used in the treatment of pain.

It is a further object of the present invention a process for preparing the compounds of formula (I).

The process, see scheme 1, comprises the following steps:
a) reaction of an aldehyde of formula 2 with an amine of formula 1 wherein $R_g$ has the meaning of methyl or benzyl, and with the 1,3-acetonedicarboxylic acid of formula 3, and obtainment of a bicyclic ketone of formula 4,
b) treatment of the ketone of formula 4 with inorganic acids in the presence of an azide, or a derivative thereof, and obtainment of the aminolactam of formula 5,
c) reduction of the aminolactam of formula 5 to obtain the diazabicyclic amine of formula 6,
d) acylation of the diazabicyclic amine of formula 6 with an alkyl anhydride, or an acyl chloride, wherein in the anhydride or in the acyl chloride the alkyl chain is $R_B$ as defined above in formula (I), obtaining the amide of formula 7, wherein the acyl substituent —C(O)—$R_B$ has the meaning of $R_1$ in formula (I),
e) hydrogenation of the amide of formula 7: by obtaining an amidic compound of formula 8,
f) substitution of the hydrogen present on the amine nitrogen of the compound of formula 8 with the substituent R as defined in formula (I), and obtainment of the compound of formula 9.

Scheme 1

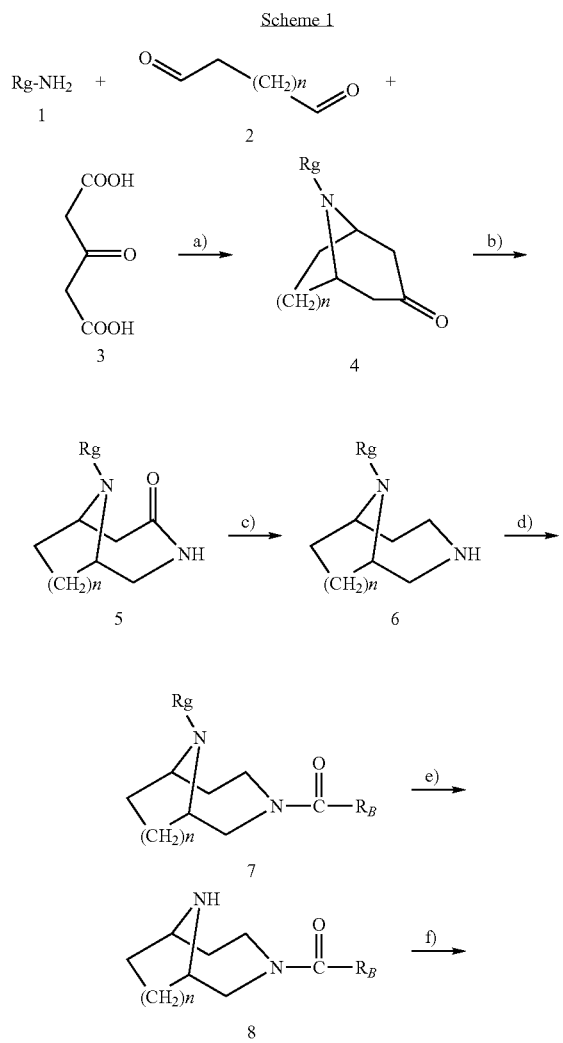

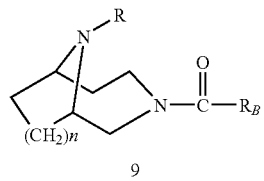

The reaction of step a) can be carried out in an aqueous solution in the presence of sodium acetate, by operating at a temperature about 0° C. The obtained mixture is left under stirring at room temperature for at least one hour and then heated to 50° C. for 3-7 hour. The pH is brought to values comprised between 4 and 5. Compound 4 is then extracted from the aqueous phase with an organic solvent, for example dichloromethane, and then recovered by solvent evaporation.

Step a) can be avoided when the ketones of formula 4 are commercially available.

In step b) the used inorganic acids, preferably concentrated, are for example sulphuric acid. Besides, the azide can be used under the form of a derivative thereof, for example $NaN_3$. Generally one operates at temperatures lower than 40° C., preferably lower than 35° C.

In step c) the reduction of the aminolactam 5 is preferably carried out with metal hydrides in an inert organic solvent, in an inert atmosphere. As metal hydride, $LiAlH_4$ can for example be used, the inert organic solvent can be for example tetrahydrofuran (THF). Generally one operates at temperatures of about 0° C. in an inert atmosphere, for example by using argon.

In step d) the acylation reaction of the diazabicyclic amine is preferably carried out in the presence of an acceptor of protons, such as a tertiary amine.

Step e) of the hydrogenation of the amide of formula 7 can be carried out by using 2,2,2-trichloro ethylchloroformate and metal zinc in acetic acid, or by catalytic hydrogenation with Pd/C.

Step f) can be carried out for example by reaction of the amine nitrogen of the compound of formula 8 with, a compound of formula R—X wherein X is a leaving group, preferably selected from halogen, mesyl or tosyl. In place of the compound R—X, an aldehyde having formula $R_T$—C(O)H can be used. The substituent $R_T$—$CH_2$—, which is formed in the reaction by using the aldehyde, corresponds to group R of formula (I). The reaction conditions are those known in the prior art. The reactants R—X are generally commercially available or can be prepared according to the processes of the prior art. For example they can be obtained by synthesis schemes as reported hereinunder.

Scheme 1'

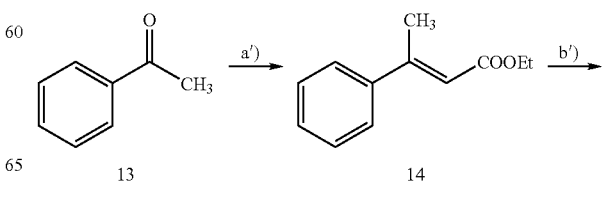

-continued

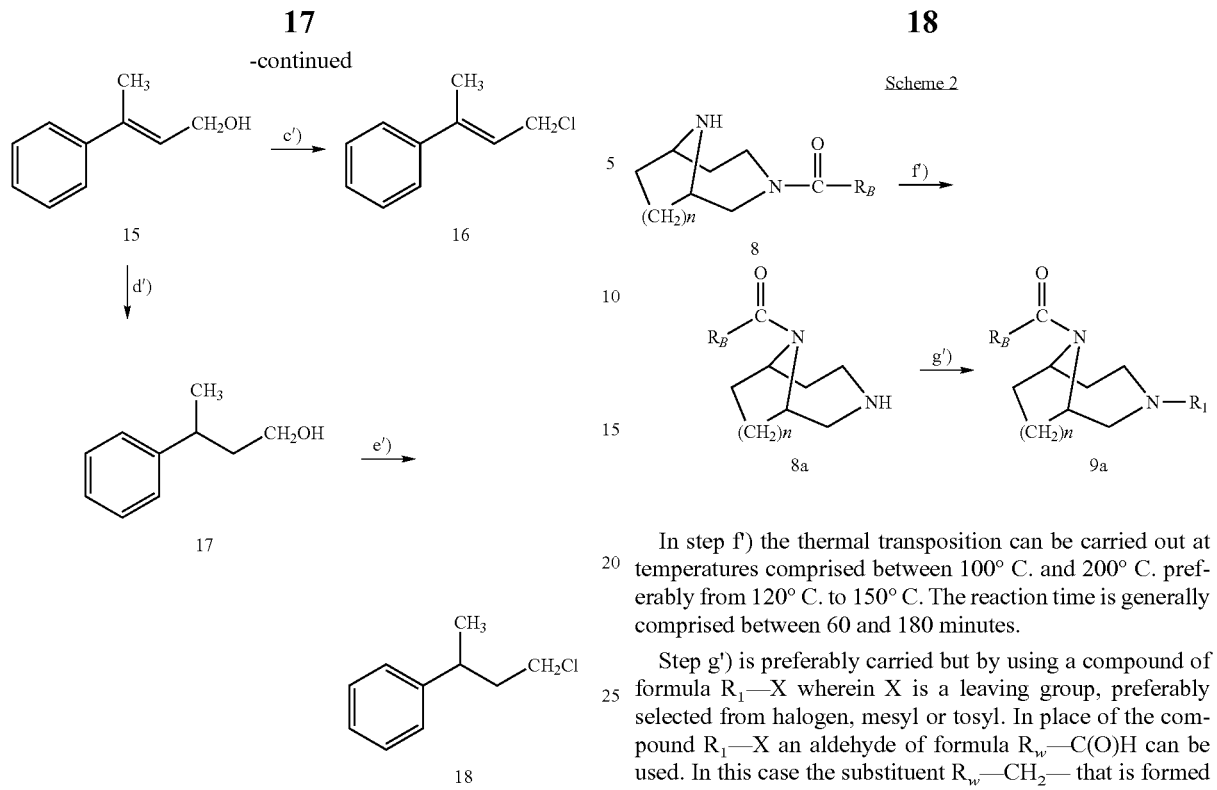

According to scheme 1', chlorides of formula 16 and 18 are obtained by the following steps:

a') 1.5 equivalents of triethyl-phosphonium acetate in toluene are reacted at room temperature with 1.5 equivalents of sodium hydride, for one hour. One equivalent of the ketone of formula 13 dissolved in toluene is dropwise added to the obtained mixture. The obtained mixture is reacted at room temperature under stirring for two-three days, obtaining the ester of the acrylic acid derivative of formula 14, b') the ester of the acrylic acid derivative of formula 14 is reduced to the corresponding alcohol of formula 15, preferably by using metal hydrides, for example $LiAlH_4$, c') the alcohol of formula 15 is halogenated preferably by treatment with concentrated hydrochloric acid, obtaining the corresponding chloride of formula 16, d') alternatively to step c'), the alcohol of formula 15 can be transformed into the corresponding alcohol of formula 17 having a saturated aliphatic chain, for example by catalytic hydrogenation with Pd/C, e') the alcohol of formula 17 is treated with concentrated HCl obtaining the chloride of formula 18.

According to an alternative process for the synthesis of the compounds of formula (I), compound 8 of scheme 1, instead of being subjected to step f), is subjected to steps f') and g'), see scheme 2:

f') obtainment of the diazabicyclic compounds of formula 8a, wherein the acyl substituent —C(O)—$R_B$ of the amidic nitrogen has the meaning of R in formula (I), by subjecting the amidic compounds of formula 8 to thermal rearrangement, g') obtainment of the compound of formula 9a by substitution of the hydrogen present on the aminic nitrogen of the compound of formula 8a with the substituent $R_1$ as defined in formula (I).

In step f') the thermal transposition can be carried out at temperatures comprised between 100° C. and 200° C. preferably from 120° C. to 150° C. The reaction time is generally comprised between 60 and 180 minutes.

Step g') is preferably carried but by using a compound of formula $R_1$—X wherein X is a leaving group, preferably selected from halogen, mesyl or tosyl. In place of the compound $R_1$—X an aldehyde of formula $R_w$—C(O)H can be used. In this case the substituent $R_w$—$CH_2$— that is formed corresponds to the group $R_1$ of formula (I). The reaction conditions of this step are those known in the prior art. The compounds $R_1$—X are generally commercially available or can be prepared according to known synthesis schemes of the prior art. See for instance scheme 1'.

According to a further alternative of the process described for the synthesis of the compounds of formula (I), instead of steps d)-f) of scheme 1, steps from g) to k) can be used according to scheme 3 reported herein below:

g) protection of the nitrogen atom at position 3 of the diazabicyclic amine of formula 6 obtaining the compound of formula 10 h) hydrogenation of the compound of formula 10, obtaining the diazabicyclic aminocarbamate compound of formula 11 i) acylation of the diazabicyclic amine of formula 11 with an alkyl anhydride, or an acyl chloride, wherein in both compounds the alkyl group is $R_B$ as defined in formula (I), and obtainment of the amide of formula 12, wherein the acyl substituent —C(O)—$R_B$ of the amidic nitrogen has the meaning of R in formula (I), j) deprotection of the amine group, obtaining the compound of formula 8a, k) obtainment of compound 9a by performing the reaction described in step g').

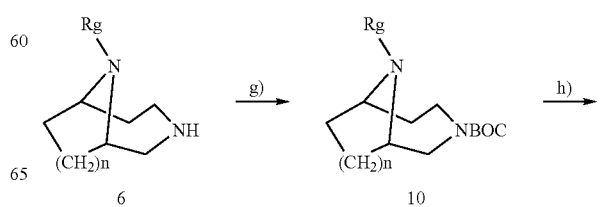

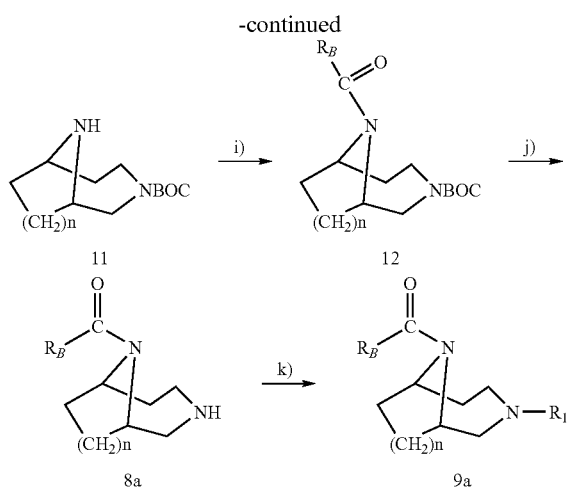

In step g) protection of the nitrogen atom is preferably carried out with di-tert-butyldicarbonate ((BOC)₂O)) in an inert solvent.

In step h) the hydrogenation reaction is carried out with Pd/C catalyst.

In step j) deprotection is carried out by treatment with trifluoroacetic acid inert solvent. This is particularly used when the amine has been protected with BOC.

The present invention relates furthermore to the compounds of formula (I) for preparing pharmaceutical compositions for the therapy and prophylaxis in mammals and in human beings of diseases and disorders wherein the opioidergic receptors μ and/or δ and/or k and/or their receptorial subclasses are involved.

An object of the present invention are the pharmaceutical compositions of the compounds of formula (I).

In the pharmaceutical compositions the compounds (I) are contained in an amount such that the active principle is in the amount required for the specific pharmaceutical application.

In the pharmaceutical compositions the compound of formula (I) can be present as such or in the form of salt or solvate, or also as isomer, as for example cis or trans isomer, or optical isomer when it contains one or more chiral centres.

The additives contained in the pharmaceutical compositions are excipients, carriers, dyestuffs, preservatives, aromas, etc., the use of which in pharmaceutical field is known. The used amounts of these various additives and excipients are those known for the specific applications.

The administration of the pharmaceutical compositions can be made by oral, subcutaneous, sublingual, intramuscular, intravenous, topic, transdermal, rectal, ophthalmic, intranasal, vaginal, intraperitoneal route.

The pharmaceutical compositions of the present invention comprise for example dispersions, solutions, emulsions, powders, capsules, aerosol, suppositories, tablets, syrups, elixirs, creams, gels, ointments, plasters, etc. See for example those described in patent application WO 2004/011,468. The pharmaceutical compositions can be obtained according to known processes of the pharmaceutical art. For example, the pharmaceutical compositions can be obtained according to processes mentioned in U.S. Pat. No. 6,028,084.

The pharmaceutical compostions can also be prepared by using the methods and the additives mentioned in patent application US 2003/0003145. In these formulations sodium alkuylsulphate or another surfactant commonly used in the pharmaceutical field can be used.

For example pharmaceutical compositions, usable for the oral administration of the compounds of formula (I), their isomers or of the corresponding hydrates or solvates or pharmaceutically acceptable salts, are formed of: 0.5-20% by weight of a compound of formula (I), comprising all the various isomers and the corresponding mixtures either of a corresponding hydrate or solvate or pharmaceutically acceptable salt; 0.05-0.5% by weight of one or more surfactants, preferably sodium alkylsulphate; 2.5-10% by weight of a disgregating agent such as cellulose, sodium carboxymethylcellulose or other cellulose derivatives.

Pharmaceutical formulations, usable for both oral and intraocular administration, can include the compounds of formula (I), their isomers, their salts included, hydrates, solvates and hydroxypropylmethylcellulose. In particular they can include from 0.1 to 20% of the compounds of formula (I) and from 0.5 to 10% of hydroxypropylmethylcellulose (HPMC).

Specific pharmaceutical formulations for the oral administration under the form of capsules or tablets, besides the compounds of formula (I) and hydroxypropylmethyl cellulose, can include other excipients, such as monohydrate lactose, magnesium stearate, microcrystalline cellulose, titanium oxide. In these preparations HPMC can be present in the core of the capsules or tablets, and/or in the tablet shell, when present.

Further formulations of the compounds of formula (I) include oil emulsions in water, wherein the active principle as such, or solubilized in an organic phase, is dispersed in an aqueous phase by using one or more amphiphilic compounds. The latter are for example surfactants, polymers soluble in oil or in water capable of forming organized structures such as aggregates, micelles, liquid crystals and vesicles in the liquid wherein they are solubilized. The emulsions can be prepared for example by means of high-pressure turboemulsifiers or homogenizers. Said emulsions generally contain (% by weight):

from 0.005 to 20% of compounds of formula (I)
from 0 to 50% of one or more oils
from 0.01 to 50% of one or more amphiphilic compounds
from 0 to 50% of additives
water or a saline aqueous solution, optionally buffered, the complement to 100%.

Other pharmaceutical formulations comprising the compounds of formula (I) are those formed of micro- and/or nano-particles of lipids or of pharmaceutically acceptable polymers wherein the compounds of formula (I), present in concentrations between 0.1 and 60% by weight with respect to the lipid or to the polymer, are incorporated inside and/or on the surface of the particles.

In the case of lipidic particles, those based on fatty acids or esters thereof having a melting point higher than 40° C., more preferably higher than 50° C., can for example be mentioned. The triglycerides of fatty acids, as tripalmitine and lanolin can for example be mentioned. The particles can also be made of mixtures between fatty acid or fatty acid ester having a melting point higher than 40° C. and a liquid oil at room temperature (20-25° C.), as for example medium chain triglycerides, as vegetable oils, Miglyol® 812 and Miglyol® 810 commercialized by Sasol. Alternatively these particles can be made of a surface layer of soya lecithin enclosing a liquid lipidic core, formed for example of medium chain triglycerides, as the vegetable oils Miglyol® 812 and Miglyol® 810.

In the case of polymeric particles, there can be mentioned those formed of: natural polymers, such as proteins, as albumin, polysaccharides, as chitosan and dextran, synthetic polymers, such as polyorganophosphazenes, polyanhydrides, polyamides, polyorthoesters and polyalkylcyano-acrylates, polyesters as polylactate (PLA) and polylactate/-polyglycolate (PLA/PLGA) copolymers, the latter group being that preferred.

The particles containing the compounds of formula (I) can optionally be modified on the surface for making the passage easier through the physiological barriers, as for example the haematoencephalic barrier, and/or for increasing the residence time in circulation of the compounds of formula (I). The particle surface modification can be carried out both by chemico-physical adsorption of one or more surface modifiers, and by chemical functionalization of the polymer with one or more specific modifiers. In the latter case the modifiers are linked by covalent bond to the particles. See for example E. Garcia et Al., "Colloidal carriers and blood-brain barrier (BBB) translocation: A way to deliver drugs to the brain", Int. J. of Pharmaceutics 298 (2005), 274-292.

Among the modifiers, there can for example be mentioned: compounds' including polyoxyethylenic or peghilated chains (PEG-based chains), as Tween 80, see for example J. Kreuter, "Nanoparticulate systems for brain delivery of drugs", Advanced Drug Delivery Reviews, 47, 2001, 65-81, M. T. Peracchia et al., "Synthesis of a Novel Poly(MePEG cyanoacrylate-co-alkyl cyanoacrylate) amphiphilic copolymer for nanoparticle technology", Macromolecules, 30, 1997, 846-851, proteins, as for example plasmatic proteins, for example apolipoproteins can be mentioned, see US 2004/0131692, antibodies, compounds which are recognized by specific receptors expressed at the level of the physiological barriers, such as peptide compounds, proteins, synthesis or natural compounds having a structure different from the peptide one. See for example L. Costantino et al., "Peptide-derivatized biodegradable nanoparticles able to cross the blood-brain barrier", Journal of Controlled Release, 108, 2005, 84-96, B. Stella et al., "Design of folic acid-conjugated nanoparticles for drug targeting", J. of Pharmaceutical Sciences 89 11, November 2000 1452-1464.

The modifiers of the particle surface can directly be linked to the main structure of the polymer, as for example in the case of PEG chains of the poly(MePEGcyanoacrylate-co-alkyl cyanoacrylates) particles described in M. T. Peracchia et al., "Synthesis of a Novel Poly(MePEG cyanoacrylate-co-alkyl cyanoacrylate) amphiphilic copolymer for nanoparticle technology", Macromolecules, 30, 1997, 846-851.

The modifiers of the particle surface can also be covalently linked to the polymer by linker having main structure comprising saturated or unsaturated alkyl chains, linear or branched, and/or aromatic and/or polyoxyethylene chains or PEG. Preferably the linker is formed of polyoxyethylene chains. The linker-polymer and linker-surface modifier bonds can be both direct bonds (C—C) and bonds formed of functional groups such as ether, amide, ester, urethane, peptide, urea groups.

The above mentioned amphiphilic compounds are selected from the following classes:
surfactants selected from non-ionic, anionic, cationic and amphoteric surfactants, optionally containing fluorine atoms,
polymers forming organized structures as aggregates, micelles, liquid crystals, vesicles, in the liquid wherein they are solubilized.

The preferred surfactants are the non-ionic and anionic ones. Among the non-ionic surfactants, the most preferred are those containing polyoxyalkylene chains, preferably polyoxyethylene chains. The following ones can for example be mentioned:

polyoxyl 35 castor oil, known for example with the commercial name Cremophor® EL (BASF), produced by ethoxylation of castor oil, polyoxyl 40 hydrogenated castor oil, known for example with the commercial name Cremophor® RH40 (BASF), produced by ethoxylation of hydrogenated castor oil, polyethylenglycol 15 hydroxystearate, known for example with the commercial name Solutol® HS15 (BASF), produced by reaction of 15 moles of ethylene oxide with 1 mole of 12-hydroxystearic acid, polyoxyethylene polysorbate, such as Tween® 80, Tween® 20, Tween® 60, Tween® 85, sorbitan esters of fatty acids, as sorbitan monolaurate and sorbitan monostearate, commercialized for example with the name Span® 20 and Span® 60, respectively, vitamin E/TPGS: tocopheryl propylenglycol 1000 succinlnate, polioxyethylen ethers of fatty acids, as those of the series Brij®, quali Brij® 35, Brij® 76, Brij® 98, PEG-12-acyloxy-stearates, see for example C. E. McNamee et al. in: "Physicochemical: Characterization of PEG 1500-12-acyloxy-stearate micelles and liquid crystalline phases", Langmuir, 2005, 21, 8146-8154, among the polyoxyethylene ethers the following can for example be mentioned:

PEG 1500 mono-12-capryloyloxy stearate (PEG 1500-$C_{18}C_8$)

PEG 1500 mono-12-caproyloxy stearate (PEG 1500-$C_{18}C_{10}$)

PEG 1500 mono-12-lauroyloxy stearate (PEG 1500-$C_{18}C_{12}$)

PEG 1500 mono-12-myristoyloxy stearate (PEG 1500-$C_{18}C_{14}$)

PEG 1500 mono-12-palmitoyloxy stearate (PEG 150-$C_{18}C_{16}$).

Among the anionic surfactants the following can for example be mentioned: soya lecithin, for example known with the commercial name Epikuron® 200, bis-2-ethylhexylsulphosuccinate (AOT), sodium taurocholate.

Among cationic surfactants, hexadecyltrimethylammonium bromide (CTAB) and didodecylammonium bromide (DDAB) can for example be mentioned.

The polymers which can be used as amphiphilic compounds must be soluble in the aqueous phase and/or in the oily phase. By "soluble" it is meant that the polymers must reach in the phase in which they are soluble concentrations at least equal to those allowing the formation of organized structures as aggregates, micelles, liquid crystals, vesicles. The presence of the above mentioned organized structures may be assessed by specific techniques of the physical chemistry of the dispersed systems, as for example Laser Light Scattering (LLS), Neutron Scattering, microscopy.

The polymers can be used also in combination with the above mentioned surfactants. Also in this case the concentration of the solubilized polymer in the used liquid phase must be such to lead to the formation of the above mentioned organized structures.

The polymers can be for example polyvinylpyrrolidone and vinylpyrrolidone/vinyl acetate copolymers, commercialized for example with the name Kollidon®, as Kollidon® 12 PF and Kollidon® 17PF (BASF), and the block copolymers containing polyoxyalkylene chains, more preferably containing polyoxyethylene chains (PEO), as for example the block copolymers PEO with polyoxypropylene chains (PPO) characterized by PEO-PPO-PEO structures, commercially available for example with the trademark Pluronico® or Poloxamer® or Lutrol®, as: Lutrol® F68 and Lutrol® F127 commercialized by Basf.

The oils usable for preparing emulsions or as lipids in the particles are selected from the following classes of pharmaceutically acceptable compounds:

esters of $C_4$-$C_{32}$ acids, optionally containing one or more unsaturations of ethylene type, $C_4$-$C_{32}$ acids optionally containing one or more ethylenic unsaturations, which are used when the final composition has a pH such that it does not transform the acid into the corresponding salt.

The esters of the acids are; preferably obtained by esterification of the corresponding acid with an alcohol having an aliphatic chain, preferably $C_1$-$C_5$, or having a polyoxyethylene chain, or with glycerine. In this case mono-, di- or triglycerides can be respectively obtained.

The following can for example be mentioned:
Oleoyl macrogol 6 glyceride (unsaturated polyglycosylated glyceride), commercialized for example with the trademark Labrafil® 1944 CS, (Gattefossé), propylenglycol caprylate caprate, known for example with the trademark Labrafac® PG (Gattefossé),
propylenglycol monoester of the caprylic acid, commercialized for example with the trademark Capmul® PG-8 (Abitec),
glycerol oleate (for example Peceol® (Gattefossé)),
medium chain mono- and diglycerides, for example capric and caprylic acid glycerides (for example Capmul® MCM (Abitec), Imwitor® 308 (Sasol)),
polyglycerol oleate (for example Pluro® oleic (Gattefossé)),
capric/caprylic acid triglycerides (for example Miglyoil® 812 and Miglyol® 810 (Sasol), Labrafac® CC CS (Gattefossé)),
ethyl butyrate, ethyl caprylate, ethyl oleate,
tripalmitine, commercialized for example with the trademark DYNASAN® 116 by Sasol.

Vegetable oils of pharmaceutical purity, containing one or more of the above; mentioned esters can also be used. Soya oil can for example be mentioned.

As fatty acid, stearic acid can be mentioned.

As additives of the emulsions, one or more compounds selected from the following classes can be used:
modifiers of the water and/or oil polarity,
modifiers of the curvature of the film of component S),
co-surfactants.

The modifiers of the water and/or oil polarity can be for example polyethylenglycols. Lutrol® E300 and Lutrol® E400 (BASF) can for example be mentioned. Aliphatic alcohols, as ethanol, can also be used.

The modifiers of the curvature of the film of component S) are for example aliphatic alcohols, preferably $C_2$-$C_5$.

The co-surfactants can for example be surfactant compounds as defined above, or aliphatic alcohols, preferably having one chain with at least 6 carbon atoms. It can for example be mentioned:
propylen glycol monolaurate, known with the commercial name Capmul® PG12 (Gattefossé) or Lauroglycol® 90 (Gattefossé),
capryloylcaproyl macrogol 8 glyceride (saturated ethyldiglycosylated glyceride) commercialized for example by the trademarks Labrasol®, Gelucire 44-14 (Gattefossé).
diethylenglycol monoethyl ether, known for example with the commercial name Transcutol® (Gattefossé).

The compounds of formula (I), comprising the various isomers and related mixtures and the corresponding hydrates or solvates and pharmaceutically acceptable salts and the pharmaceutical compositions thereof, have a high affinity in vitro for the opioidergic receptors μ and/or δ and/or k, and/or all their receptorial subclasses. See the examples. More specifically the compounds of formula (I) have a Ki value for the opioidergic receptors μ and/or δ and/or k, lower than 0.5 μM.

It is a further object of the present invention the use of the compounds of formula (I) and of the pharmaceutical compositions containing them for the prophylaxis and therapy in mammals and in human beings of diseases and disorders wherein the opioidergic receptors μ and/or δ and/or k and/or their receptorial subclasses are involved.

The diseases and disorders which can be treated with the compounds of formula (I) and with the pharmaceutical compositions containing them are: pain, post surgery pain, chronic pain, neuropathic pain, treatment of cases of abuse substances (as for example heroin and cocaine abuse), alcoholism, constipation, diarrhea and other disorders of the gastrointestinal tract, nausea, vomit, dermatitis, obesity and other disorders connected with appetite, depression, smoke dependence (tabagism), sexual disfunctions, shocks, cerebral trauma, spinal damages and eye pathologies and disorders as for example glaucoma and intraocular hypertension, tumours as for example breast cancer.

The use of the pharmaceutical compositions of the present invention for the treatment of the various pathologies can be made by: using the known methods employed for said treatments.

In particular the administration of the compositions of the invention must be carried out so that the amount of active principle is effective for the specific treatment. The dosages, the administration routes and the posologies are set depending on the type of disease, its severity, the physical conditions and characteristics of the patient, such as age, weight, response to the active principle, the pharmacokinetics and toxicology of the active principle for the specific treatment.

The preferred daily dosage is 0.01-1,000 mg of compound of formula (I) per Kg of weight of mammals to be treated. In the case of human beings, the preferred daily range is 0.1-800 mg of compound for Kg/weight, still more preferred from 1 to 600 mg.

The compounds of formula (I), containing radioactive isotopes and the pharmaceutical formulations thereof, can be used for identifying and marking the opioidergic receptors μ and/or δ and/or k and/or all their receptorial subclasses in mammals or in human beings.

Furthermore the compounds of formula (I) containing one hydroxyl group, can be used to obtain ligands. The ligands are detectable by immunochemical methods, and are used in the separation, purification and characterization of the opioidergic receptors μ and/or δ and/or k and/or the receptorial subclasses thereof and in the identification of the corresponding; active sites.

As said, the compounds of formula (I) and the pharmaceutical compositions containing them show a better tolerance with: respect to morphine. The pharmaceutical compositions containing the compounds of formula (i) are able to provide a high bioavailability of the active principles in the treatment of the above mentioned pathologies.

The following examples are given for a better understanding of the present invention but are not meant to be limitative of the scope of the invention.

EXAMPLES

Example 1

Synthesis of the compound 9-methyl-3,9-diazabicyclo[4.2.1]nonan-4-one

To a solution (5 g) in chloroform (50 ml) of tropinone (1a) of formula:

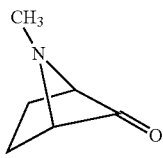

(1a)

cooled at −5° C., 11.3 ml of conc. H₂SO₄ are dropwise added while maintaining the temperature lower than 15° C. NaN₃ (4.67 g) is then slowly added in small amounts lumpwise so to avoid temperatures exceeding 35° C. Then it is heated at reflux for two hours. The obtained mixture is poured in a vessel containing about 200 ml of ice. Solid K₂CO₃ is added up to obtain a strongly alkaline pH. An emulsion is formed. 25 ml of 60% aqueous KOH are added to said emulsion. It is left under stirring for 10 minutes, then the formed inorganic salts are filtered and the reaction mixture is extracted with chloroform. The organic phase is anhydrified on sodium sulphate and the solvent evaporated to obtain 3.64 g of compound 9-methyl-3,9-diazabicyclo-[4.2.1]nonan-4-one (1b) as a white crystalline solid.

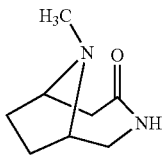

(1b)

Yield: 95%; R_f: 0.26 (CHCl₃-MeOH 8:2); m.p.: 79-82° C.; ¹H-NMR (CDCl₃): δ (ppm) 1.69-1.85 (m, 2H), 2.00-2.20 (m, 2H), 2.42 (s, 3H), 2.48-2.53 (m, 1H), 2.80-2.96 (m, 2H), 3.15-3.27 (m, 2H), 3.59 (bd, 1H, J=14 Hz).

Example 2

Synthesis of 9-methyl-3,9-diazabicyclo-[4.2.1]nonane

To a suspension of LiAlH₄ (0.61 g) in anhydrous THF (30 ml), cooled at 0° C., and kept under an argon inert atmosphere, a solution in THF of 9-methyl-3,9-diazabicyclo [4.2.1]nonan-4-one obtained in example 1 is dropwise added (1.00: of compound in 10 ml of THF). The obtained mixture is heated at reflux for 48 hours and then cooled at 0° C. Then water (3 ml) is slowly added to the mixture. After water addition, the mixture is kept under stirring for 1:0 minutes. A precipitate is formed, that at the end is filtered under vacuum and washed with dichloromethane. The obtained filtrate is evaporated obtaining an oil which is dissolved in dichloromethane. The obtained solution is then anhydrified on sodium sulphate and the solvent evaporated. The residual oil is distilled (45-50° C./0.1 mmHg) to give 0.63 g of 9-methyl-3,9-diazabicyclo[4.2.1]nonane (2a) as a colourless oil.

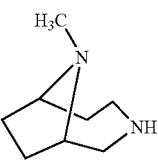

(2a)

Yield: 69%; R_f: 0.22 (CHCl₃-MeOH 9:1+drop of NH₄OH); b.p.: 45-50° C./0.1 mmHg; ¹H-NMR (CDCl₃): δ (ppm) 1.40-2.38 (m, 4H), 2.05-2.15 (m, 2H), 2.44 (s, 3H), 2.47 (bs, 1H, NH), 2.64-3.30 (m, 6H); ¹³C-NMR (CDCl₃): δ (ppm) 28.16; 30.65; 37.30; 43.69; 45.84; 55.57; 63.98; 66.69.

Example 3

Synthesis of 3-propionyl-9-methyl-3,9-diazabicyclo[4.2.1]nonane

To a solution in anhydrous dichloromethane (18 ml) of 9-methyl-3,9-diazabicyclo[4.2.1]nonane obtained in Example 2 (0.63 g), cooled at 0° C., a propionic anhydride solution (2.1 ml) in anhydrous dichloromethane (5 ml) is added. The obtained mixture is heated at reflux for one hour, then cooled to room temperature, made alkaline, with a NaOH aqueous solution at 40% w. and left under stirring for 16 hours. The so obtained mixture is extracted with dichloromethane; the organic phase is separated, anhydrified on sodium sulphate and evaporated. 0.88 g of compound 3-propionyl-9-methyl-3,9-diazabicyclo[4.2.1]nonane (3a) are obtained under the form of a light yellow oil. The yield is quantitative.

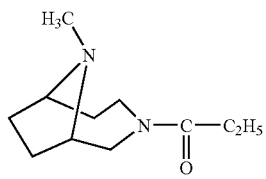

(3a)

R_f: 0.44 (CH₂Cl₂-MeOH 9:1); ¹H-NMR (CDCl₃): δ (ppm) 1.16 (t, 3H, J=7.4 Hz), 1.21-2.38 (m, 6H), 2.43 (s, 3H), 2.80-2.88 (m, 1H), 3.19-3.75 (m, 5H), 3.85-4.00 (m, 1H), 4.35 (bd, 1H, J=14 Hz).

Example 4

Synthesis of 3-propionyl-3,9-diazabicyclo-[4.2.1]nonane

To a solution in toluene (25 ml) of 3-propionyl-9-methyl-3,9-diaza-bicyclo[4.2.1]nonane obtained in Example 3 (0.49 g), kept under an argon inert atmosphere, 0.4 ml of 2,2,2-trichloroethylchloroformate and 0.52 g of K₂CO₃ are added. The mixture is heated at reflux for 16 hours, then cooled at room temperature, washed with water, then with an aqueous solution of citric acid at 15% and brine. The organic phase recovered at the end of the washings is anhydrified on sodium sulphate and the solvent evaporated, obtaining 0.76 g of a yellow oil (carbamate). The oil is dissolved in 25 ml of glacial acetic acid. 0.82 g of zinc in powder are added to the so obtained solution. The mixture is kept under stirring at room temperature for 16 hours and then diluted with about 25 ml of toluene, and finally evaporated under vacuum. The residue is dissolved in a minimum volume of dichloromethane and extracted three times with an aqueous solution of citric acid at 15% w. The aqueous phases are washed with dichloromethane, then made alkaline with conc. NH₄OH and extracted again with dichloromethane. The organic phase is anhydrified on sodium sulphate and the solvent evaporated to obtain 0.28 g of the compound 3-propionyl-3,9-diazabicyclo[4.2.1]nonane (4a) as a yellow oil.

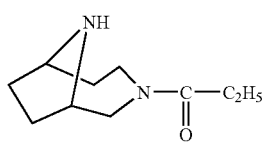

(4a)

Yield: 62%; $R_f$: 0.15 ($CH_2Cl_2$-MeOH 9:1); ¹H-NMR ($CDCl_3$): δ (ppm) 1.16 (t, 3H, J=7.6 Hz), 1.25-2.00 (m, 6H), 2.06 (bs, 1H, NH), 2.20-2.48 (m, 2H), 2.75-2.85 (m, 1H), 3.25-4.03 (m, 4H), 4.39 (bd, 1H, J=14 Hz).

Example 5

Synthesis of 9-propionyl-3,9-diazabicyclo-[4.2.1]nonane 0.55 g of the compound 3-propionyl-3,9-diazabicyclo[4.2.21]nonane obtained in Example 4 are heated to 110° C. for one hour. The residue is purified by flash chromatography ($CH_2Cl_2$-MeOH 8:2) obtaining 0.21 g of the compound 9-propionyl-3,9-diazabicyclo[4.2.1]nonane (5a)

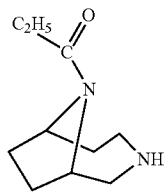

(5a)

Yield: 42%; $R_f$: 0.17 ($CH_2Cl_2$-MeOH 8:2); ¹H-NMR ($CDCl_3$): δ (ppm) 1.16 (t, 3H, J=7.6 Hz), 1.20-2.65 (m, 9H), 2.46 (bs, 1H, NH), 2.70-3.10 (m, 3H), 4.13-4.30 (m, 1H), 4.60-4.73 (m, 1H).

Example 6

Synthesis of 9-benzyl-9-azabicyclo[3.3.1]nonan-3-one

To a solution in water (400 ml) of pentandial (84.5 g) and benzylamine hydrochloride (36.3 g), cooled at 0° C. 30.8 g of 1,3-acetonedicarboxylic acid are added. 70 ml of an aqueous solution of sodium acetate at 10% are then added. The obtained mixture is kept under stirring at room temperature for one hour and then heated for 4 hours at 50° C. The mixture is then acidified at pH 2 with a 10% w. HCl aqueous solution and then washed with diethyl ether. The pH is then brought to 6 with sodium bicarbonate and the aqueous phase extracted with dichloromethane. The organic extracts are anhydrified on sodium sulphate and the solvent evaporated to obtain 38.5 g of the compound 9-benzyl-9-azabicyclo[3.3.1]nonan-3-one (6a) as a light coloured solid.

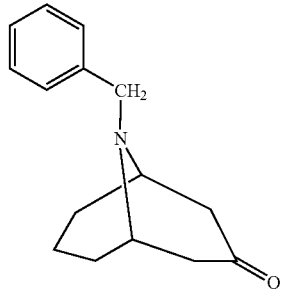

(6a)

Yield: 78%; B.p. 165-169° C./0.2 mmHg; ¹H-NMR ($CDCl_3$). δ (ppm) 1.49-1.59 (m; 6H), 2.26 (d, 2H, J=19 Hz), 2.76 (dd, 2H, J=8 and 19 Hz), 3.28-3.49 (bs, 2H), 3.91 (s, 2H), 7.22-7.46 (m, 5H).

Example 7

Synthesis of 10-benzyl-3,10-diazabicyclo-[4.3.1]decan-4-one

To a solution of 9-benzyl-9-azabicyclo[3.3.1]nonan-3-one (0.5 g) in chloroform (4.4 ml), cooled at −5° C., 1 ml of conc. $H_2SO_4$ is dropwise added, while maintaining the temperature under 15° C. $NaN_3$ (0.28 g) is then slowly added in small amounts each time, so to avoid that the reaction temperature exceeds 35° C. It is then heated at reflux for 2 hours; the obtained mixture is poured into a vessel containing about 200 ml of ice. Solid $K_2CO_3$ is added up to have a strongly alkaline pH. An emulsion is formed, to which 25 ml of a KOH aqueous solution at 60% are added. It is left under stirring for 10 minutes, then the formed inorganic salts are filtered off and an extraction with chloroform is effected. The organic phase is anhydrified on sodium sulphate and the solvent evaporated to obtain 0.50 g of 10-benzyl-3,10-diazabicyclo[4.3.1]decan-4-one (7a) as a light solid,

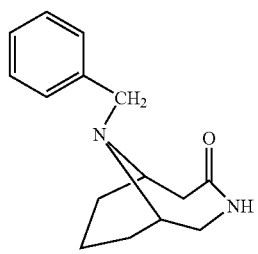

(7a)

Yield: 95%; $R_f$: 0.42 ($CHCl_3$-MeOH 97:3); ¹H-NMR ($CDCl_3$): δ (ppm) 1.43-1.70 (m, 3H). 1.90-2.23 (m, 3H) 2.37-2.53 (m, 1H), 2.80-3.15 (m, 4H), 3.75 (dt, 1H, J=3.8 and 15 Hz), 3.93 (s, 2H), 5.82 (bs, 1H), 7.20-7.40 (m, 5H).

Example 8

Synthesis of 10-benzyl-3,10-diazabicyclo-[4.3.1]decane

To a suspension of $LiAlH_4$ (0.19) in anhydrous THF (9 ml), cooled at 0° C., kept under an argon inert atmospheres a solution of 10-benzyl-3,10-diaza-bicyclo[4.3.1]decan-4-one obtained in Example 7 (0.50 g) in THF (4 ml) is dripped, The mixture is kept under stirring at room temperature for 14 hours. The mixture is then cooled at 000, about 0.9 ml of H₂O are added with caution, leaving afterwards under stirring for 10 min. The obtained precipitate is filtered under vacuum and washed with dichloromethane. The filtrate is evaporated, the obtained oil is dissolved in dichloromethane, the solution is anhydrified with sodium sulphate and the solvent evaporated to give 0.47 g of the compound 10-benzyl-3,10-diazabicyclo[4.3.1]decane (8a).

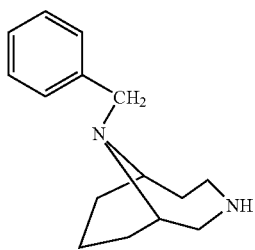
(8a)

Yield: quantitative; $R_f$: 0.62 (CH₂Cl₂-MeOH 8:2); ¹H-NMR (CDCl₃): δ ((ppm) 1.17-2.18 (m, 8H), 2.62 (bs, 1H), 2.76-2.92 (m, 2H); 2.99-3.18 (m, 4H), 3.97 (s, 2H), 7.20-7.42 (m, 5H).

Example 9

Synthesis of 10-benzyl-3-propionyl-3,10-diazabicyclo[4.3.1]decane

To a solution of 10-benzyl-3,10-diazabicyclo[4.3.1]-decane obtained in Example 8 (0.63 g) in anhydrous dichloromethane (18 ml), cooled at 000, propionic anhydride (1.27 ml) dissolved in anhydrous dichloromethane (5 ml), is added. The mixture is heated at reflux for one hour, then cooled to room temperature, made alkaline with an aqueous solution of NaOH at 40% and left under stirring for 16 hours. The mixture is extracted with dichloromethane, the organic phase separated, anhydrified on sodium sulphate and evaporated. 0.73 g of the compound 10-benzyl-3-propionyl-3,10-diazabicyclo[4.3.1]decane (9a) are obtained as a light yellow oil.

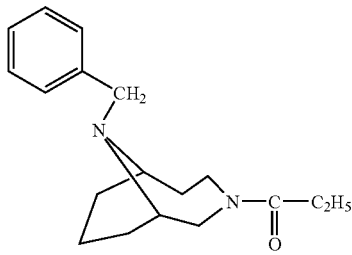
(9a)

Yield: 94%; $R_f$: 0.55 (AcOEt-ligroin 6:4); ¹H-NMR (CDCl₃): δ (ppm) 1.05-1.30 (m, 3H), 1.38-2.13 (m, 8H), 2.20-2.46 (m, 2H), 2.82-3.18 (m, 2H), 3.38-3.65 (m, 3H), 3.72-4.00 (m, 3H), 7.1:5-7.40 (m, 5H).

Example 10

Synthesis of 3-propionyl-3,10-diazabicyclo-[4.3.1]decane

A solution in EtOH (39 ml) of 10-benzyl-3-propionyl-3,10-diaza-bicyclo[4.3.1]decane obtained in Example 9 (2.40 g) was hydrogenated at 45 psi and at room temperature for 19 hours in the presence of Pd/C 10% (0.89 g). The mixture was filtered off on celite and the catalyst washed with EtOH. The solution was concentrated to obtain 1.60 g of a light oil corresponding to the compound 3-propionyl-3,10-diazabicyclo[4.3.1]decane (10a).

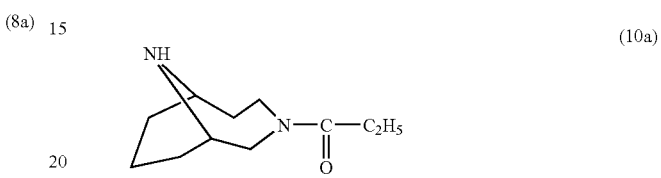
(10a)

Yield 97%; $R_f$: 0.15 (CH₂Cl₂-MeOH 9:1); ¹H-NMR (CDCl₃): δ (ppm) 1.16 (t, 3H, J=7.6 Hz), 1.35-2.09 (m, 8H), 2.38 (q, 2H, J=7.4 Hz), 2.68-2.83 (m, 2H), 3.06-3.96 (m, 5H).

Example 11

Synthesis of 10-benzyl-3-BOC-3,10-diazabicyclo[4.3.1]decane

To a solution of di-tert-butyldicarbonate (BOC) in THF (1.38 g of BOC₂O in 12 ml of THF), cooled at 0° C., a solution of 10-benzyl-3,10-diazabicyclo[4.3.1]decane obtained in Example 8 (0.97 g) in THF (8 ml) is added. The mixture is left under stirring for 10 minutes, warmed to room temperature and then left under stirring for 16 hours. The obtained solution was diluted with Et₂O and washed with an aqueous solution of NaHCO₃ at 10% and then with brine. The organic phase was anhydrified on Na₂SO₄ and concentrated. The obtained residue was, purified by flash chromatography (ligroin/Et₂O 9:1). 1.11 g of the compound 10-benzyl-3-BOC-3,10-diazabicyclo[4.3.1]decane (11a) are obtained as a colourless oil.

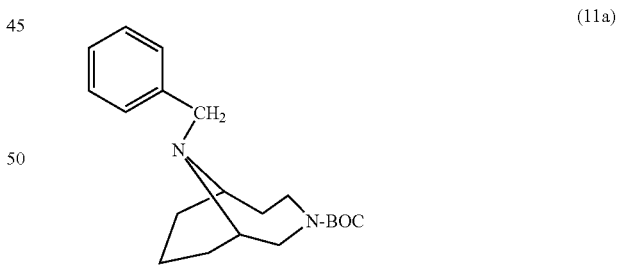
(11a)

Yield: 80%; $R_f$: 0.48 (ligroin/Et₂O 9:1); ¹H-NMR (CDCl₃): δ (ppm) 1.18-2.15 (m, 8H), 1.46 (s, 3H), 1.50 (bs, 6H): 2.80-3.00 (m, 1H), 3.05-3.22 (m, 1H) 3.23-3.90 (m, 4H), 3.92 (s, 2H), 7.20-7.50 (m, 5H).

Example 12

Synthesis of 3-BOC-3,10-diazabicyclo-[4.3.1]-decane

A solution of 10-benzyl-3-Boc-3,10-diazabicyclo-[4.3.1] decane obtained in Example 11 (3.50 g) in EtOH (52 ml)

underwent hydrogenation at 45 psi and 30° C. for 19 hours in the presence of Pd/C 10% (1.13 g). At the end the mixture was filtered on celite and the catalyst washed with EtOH. The solution was then concentrated. 2.44 g of a light oil corresponding to the compound 3-BOC-3,10-diazabicyclo[4.3.1]decane (12a) are obtained.

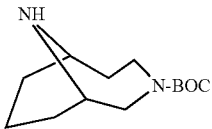

(12a)

Yield: 96%; $R_f$: 0.55 (CHCl$_3$-MeOH 9:1); —NMR (CDCl$_3$): δ (ppm) 1.38-2.00 (m, 8H), 1.48 (s, 9H), 2.30 (bs, 1H), 3.05-3.42 (m, 4H), 3.60-3.88; (m 2H).

Example 13

Synthesis of 3-BOC-10-propionyl-3,10-diazabicy-clo[4.3.1]decane

To a solution in anhydrous dichloromethane (8 ml) of 3-BOC-3,10-diazabicyclo[4.3.1]decane obtained in Example 12 (0.34 g), cooled at 0° C., propionic anhydride (0.66 ml) dissolved in anhydrous dichloromethane (3 ml), is added. The mixture is heated at reflux for one hour, then cooled to room temperature, then made alkaline with an aqueous solution of NaOH at 40% and left under stirring for 16 hours. The mixture is extracted with dichloromethane, the organic phase separated, anhydrified on sodium sulphate and evaporated to give 0.32 g of a colourless oil corresponding to 3-BOC-10-propionyl-3,10-diazabicyclo[4.3.1]decane (13a).

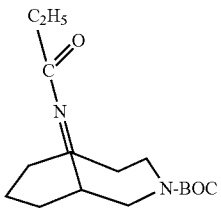

(13a)

Yield: 76%; $R_f$: 0.32 (ligroin-AcOEt 7:3); $^1$H-NMR (CDCl$_3$): δ (ppm) 1.17 (t, 3H, J=8-8 Hz), 1.44 (s, 3H), 1.48 (s, 6H), 1.50-2.60 (m, 11H), 2.90-3.20 (m, 3H), 3.82-4.40 (m, 1H), 4.73-5.17 (m, 1H).

Example 14

Synthesis of 10-propionyl-3,10-diazabicyclo-[4.3.1]decane

To a solution in dichloromethane (7 ml) of 3-BOC-10-propionyl-3,10-diazabicy-clo[4.3.1]decane obtained in Example 13 (0.32 g), cooled at 0° C., trifluoroacetic acid (0.83 ml) in 3 ml of dichloromethane, is added. The mixture is kept under stirring at room temperature for 3 hours. The solvent is then evaporated and the residue treated with an aqueous solution of saturated NaHCO$_3$, then extracted with CH$_2$Cl$_2$. The organic phase is separated, anhydrified on sodium sulphate and evaporated. 0.21 g of a light oil corresponding to the compound 10-propionyl-3,10-diazabicyclo [4.3.1]decane (14a) are obtained.

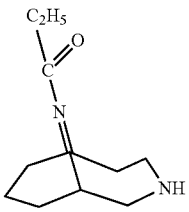

(14a)

Yield: quantitative; $R_f$: 0.20 (CH$_2$Cl$_2$-MeOH 8:2); $^1$H-NMR (CDCl$_3$): δ (ppm) 1.17 (t, 3H, J=7.2 Hz), 1.31-2.60 (m, 11H), 1.84 (bs, 1H), 2.76-3.12 (m, 3H), 3.92-4.40 (m, 1H), 4.71-5.17 (m, 1H).

Example 15

General method for preparing 3-propionyl-9-alkyl-3,9-diazabicyclo[4.2.1]nonane (I-A) Compounds A mixture formed of the compound 3-propionyl-3,9-diazabicyclo[4.2.1]nonane (4a) obtained in Example 4 (0.6 mmoles), K$_2$CO$_3$ (0.72 mmoles), acetone (7 ml) and an organic chloride (0.72 mmoles) of general formula (II-A):

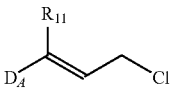

(II-A)

wherein $D_A$ and $R_{11}$ have the meanings reported in Table 1, is heated at reflux for 24 hours. The mixture is then cooled to room temperature, the formed solid filtered and acetone evaporated. The residue has been purified by flash chromatography (CH$_2$Cl$_2$/acetone 8:2) obtaining the compounds 3-propionyl-9-alkyl-3,9-diazabicyclo[4.2.1]nonanes of formula I-Aa up to I-Ad, as oils, characterized by the following general chemical structure (I-A):

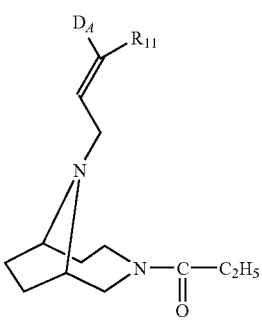

(I-A)

In Table 1 for each of the synthesized compounds I-Aa, I-Ab, I-AC and I-Ad, it is indicated: $D_A$, $R_{11}$, reaction yield in percent (Yield %), the melting point in centigrade degrees (m.p. in ° C.) of the corresponding fumarate salts, the empirical formula, the wave length (λ) of the IR band corresponding to the group —C(O)—, the significant peaks of the $^1$H-NMR analysis in CDCl$_3$ ($^1$H-NMR δ ppm).

Example 16

General method for preparing 3 alkyl-9-propionyl-3,9-diazabicyclo[4.2.1]nonanes (I-B)

The same procedure described in the preparation of 3-propionyl-9-alkyl-3,9-diazabicyclo[4.2.1]nonanes (Example 15) has been used for the preparation of 3-alkyl-9-propionyl-3,9-diazabicyclo[4.2.1]nonanes by using the compound 9-propionyl-3,9-diazabicyclo[4.2.1]nonane (5a) obtained in Example 5 instead of the compound 3-propionyl-3,9-diazabicyclo[4.2.1]nonane (4a). The compound (5a) was reacted with the organic chlorides of general formula (II-A) (see Example 15), wherein $D_A$ and $R_{11}$ have the Values reported in Table 1. In the Table the compounds 3-alkyl-9-propionyl-3,9-diazabicyclo[4.2.1]-nonanes of formula I-B: I-Ba, I-Bb, I-Bc and I-Bd which have been synthesized with this method, are reported. They are in the physical form of oils and are characterized by the general chemical structure (I-B).

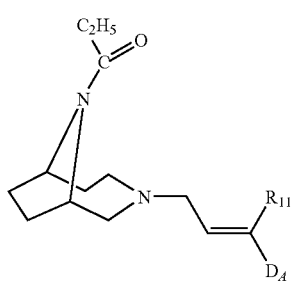

(I-B)

Example 17

General Method for the Preparation of 3-propionyl-10-alkyl-3,10-diazabicyclo[4.3.1]decanes (I-C)

The same method described in Example 15 has been used for the preparation of the compounds 3-proprionyl-10-alkyl-3,100-diaza-bicyclo[4.3.1]decanes characterized by the following general chemical structure (I-C):

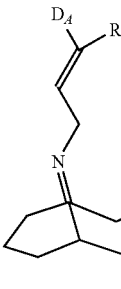
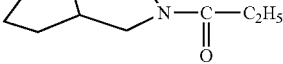

(I-C)

With respect to the Example in this case in the synthesis it is used the compound 3-propionyl-3,10-diazabicyclo[4.3.1]decane (100a) obtained in Example 10 in place of 3-propionyl-3,9-diazabicyclo[4.2.1]nonane (4a). The compounds of general formula I-C have been synthesized by using the organic chlorides of general formula (II-A), see Example 15 wherein $D_A$ and $R_1$, have the meanings reported in Table 1 for each of the compounds synthesized according to this method: I-Ca, I-Cb I-Cc.

Example 18

General Method for the Preparation of 3-alkyl-10-propionyl-3,10-diazabicyclo[4.3.1]decanes (I-D)

The same method described for the preparation of 3-propionyl-9-alkyl-3,9-diazabicyclo[4.2.1]nonanes (Example 15) is carried out, by using the compound 10-propionyl-3,1:0-diazabicyclo[4.3.1]decane (14a) obtained in Example 14 in place of the compound 3-propionyl-3,9-diazabicyclo-[4.2.1]nonane (4a). The organic chlorides used are those of general formula (II-A), wherein $D_A$ and $R_{11}$ have the meanings reported in Table 1. The obtained compounds 3-alkyl-10-propionyl-3,10-diazabicyclo[4.3.1]decanes have formula (I-D) and are in the physical form of oils.

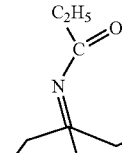
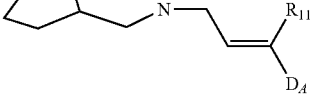

(I-D)

The following compounds: I-Da, I-Db and I-Dc are reported in the Table.

TABLE 1

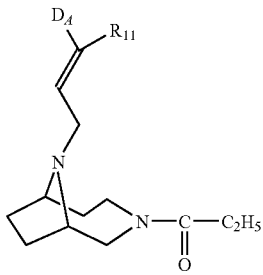

(I-A)

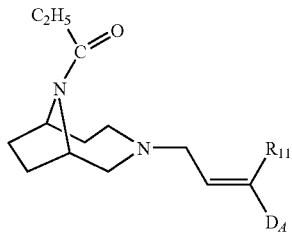

(I-B)

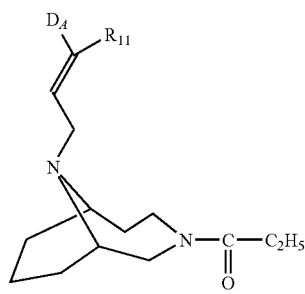

(I-C)

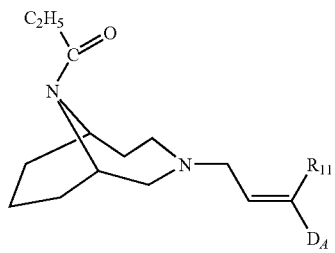

(I-D)

| Example | $R_{11}$ | $D_A$ | Yield % | m.p. (°C.) | Formula (analysis) | IR λ (cm$^{-1}$) | $^1$H-NMR δ ppm |
|---|---|---|---|---|---|---|---|
| (I-Aa) | CH$_3$ | Phenyl | 30 | 230-232 | C$_{20}$H$_{28}$N$_2$O (C, H, N) | 1658 | 1.16 (t, 3 H, J = 7.4 Hz), 1.20-2.50 (m, 7 H), 2.04 (s, 3 H), 2.79 (dd, 1 H, J = 2.6 e 13.2 Hz), 3.18-4.03 (m, 5 H), 3.35 (d, 2 H, J = 6.2 Hz), 4.40 (bd, 1 H, J = 12.4 Hz), 5.88 (t, 1 H, J = 6.0 Hz), 7.15-7.50 (m, 5 H) |
| (I-Ab) | CH$_3$ | 3,4-dichloro phenyl | 31 | 188-189 | C$_{20}$H$_{26}$Cl$_2$N$_2$O (C, H, N) | 1660 | 1.16 (t, 3 H, J = 7.6 Hz), 1.20-2.53 (m, 7 H), 2.00 (s, 3 H), 2.81 (bd, 1 H, J = 12.8 Hz), 3.12-4.04 (m, 7 H), 4.38 (bd, 1 H, J = 12.2 Hz), 5.88 (t, 1H, J = 6.0 Hz), 7.23 (d, 1 H, J = 9.0 Hz), 7.38 (d, 1 H, J = 8.2 Hz), 7.46 (s, 1 H) |
| (I-Ac) | CH$_3$ | 4-Cl-Naphthyl | 76 | 97-101 | C$_{24}$H$_{29}$ClN$_2$O (C, H, N) | 1650 | 1.16 (t, 3 H, J = 7.6 Hz), 1.36-1.88 (m, 8 H), 2.08 (s, 3 H), 2.71-2.87 (m, 1 H), 3.18-4.24 (m, 6 H), 4.43 (d, 1 H, 12.0 Hz), 5.44-5.78 (m, 1 H), 7.36-8.42 (m, 6 H) |
| (I-Ad) | Phenyl | Phenyl | 27 | 176-177 | C$_{25}$H$_{30}$N$_2$O (C, H, N) | 1659 | 1.13 (t, 3 H, J = 7.4 Hz), 1.20-2.46 (m, 7 H), 2.77 (dd, 1 H, J = 2.6 and 12.8 Hz), 3.10-4.00 (m, 5 H), 3.22 (d, 2 H, J = 6.6 Hz), 4.34 (bd, 1 H, J = 12.2 Hz), 6.20 (dt, 1 H, J = 2.2 e 6.8 Hz), 7.00-7.46 (m, 10 H) |

TABLE 1-continued

| | | | | | | |
|---|---|---|---|---|---|---|
| (I-Ba) | CH$_3$ | Phenyl | 39 | 228-230 | C$_{20}$H$_{28}$N$_2$O (C, H, N) | 1644 | 1.16 (t, 3 H, J = 7.4 Hz), 1.40-3.04 (m, 12 H), 2.04 (s, 3 H), 3.24 (d, 2 H, J = 6.6 Hz), 4.02-4.18 (m, 1 H), 4.55-4.75 (m, 1 H), 5.83 (t, 1 H, J = 6.6 Hz), 7.20-7.50 (m, 5 H) |
| (I-Bb) | CH$_3$ | 3,4-dichloro-Fenile | 29 | 186-188 | C$_{20}$H$_{26}$Cl$_2$N$_2$O (C, H, N) | 1643 | 1.16 (t, 3 H, J = 7.6 Hz), 1.40-2.83 (m, 12 H), 2.00 (s, 3 H), 3.23 (d, 2 H, J = 6.6 Hz), 4.05-4.25 (m, 1 H), 4.55-4.75 (m, 1 H), 5.83 (t, 1 H, J = 6.2 Hz), 7.20 (dd, 1 H, J = 2.2 and 8.6 Hz), 7.38 (dd, 1 H, J = 1.2 and 8.4 Hz), 7.45 (d, 1 H, J = 2.0 Hz) |
| (I-Bc) | CH$_3$ | 4-Cl-Naphthyl | 50 | 95-99 | C$_{24}$H$_{29}$ClN$_2$O (C, H, N) | 1650 | 1.22 (t, 3 H, J = 7.4 Hz), 1.20-2.00 (m, 8 H), 2.19 (s, 3 H), 2.19-2.92 (m, 4 H), 3.30 (d, 2 H. J = 7.4 Hz), 4.22-4.32 (m, 1 H), 4.58-4.68 (m, 1 H), 5.79 (m, 1 H), 7.14-8.33 (m, 6 H) |
| (I-Bd) | Phenyl | Phenyl | 41 | 184-186 | C$_{25}$H$_{30}$N$_2$O (C, H, N) | 1642 | 1.15 (t, 3 H, J = 7.4 Hz), 1.40-2.82 (m, 12 H), 3.10-3.22 (m, 2 H), 4.04-4.28 (m, 1 H), 4.55-4.75 (m, 1 H), 6.15 (t, 1 H, J = 6.6 Hz), 7.10-7.47 (m, 10 H) |
| (I-Ca) | CH$_3$ | Phenyl | 64 | 106-108 | C$_{21}$H$_{30}$N$_2$O (C, H, N) | 1640 | 1.18 (t, 3 H, J = 7.6 Hz), 1.20-2.55 (m, 10 H), 2.07 (s, 3 H), 2.87-4.34 (m, 8 H), 5.75-5.92 (m, 1 H), 7.10-7.43 (m, 5 H) |
| (I-Cb) | CH$_3$ | 3,4-dichloro phenyl | 67 | 184-185 | C$_{21}$H$_{28}$Cl$_2$N$_2$O (C, H, N) | 1655 | 1.18 (t, 3 H, J = 7.6 Hz), 1.20-2.54 (m, 10 H), 2.02 (s, 3 H), 2.83-4.13 (m, 8 H), 5.69-6.01 (m, 1 H), 7.17-7.53 (m, 3 H) |
| (I-Cc) | Phenyl | Phenyl | 68 | 137-139 | C$_{26}$H$_{32}$N$_2$O (C, H, N) | 1660 | 1.15 (t, 3 H, J = 7.6 Hz), 1.20-2.49 (m, 10 H), 2.87-4.06 (m, 8 H), 6.05-6.23 (m, 1 H), 7.08-7.44 (m, 10 H) |
| (I-Da) | CH$_3$ | Phenyl | 64 | 144-146 | C$_{21}$H$_{30}$N$_2$O (C, H, N) | 1650 | 1.17 (t, 3 H, J = 7.6 Hz), 1.34-3.00 (m, 14 H), 2.03 (s, 3 H), 3.15-3.23 (m, 2 H), 3.80-4.38 (m, 1 H), 4.60-5.17 (m, 1 H), 5.76-5.95 (m, 1 H), 7.02-7.53 (m, 5 H) |
| (I-Db) | CH$_3$ | 3,4-dichloro phenyl | 58 | 175-176 | C$_{21}$H$_{28}$Cl$_2$N$_2$O (C, H, N) | 1660 | 1.17 (t, 3 H, J = 6.2 Hz), 1.18-2.95 (m, 14 H), 1.99 (s, 3 H), 3.15-3.24 (m, 2 H), 3.80-4.40 (m, 1 H), 4.62-5.11 (m, 1 H), 5.72-5.92 (m, 1 H), 7.14-7.47 (m, 3 H) |
| (I-Dc) | Phenyl | Phenyl | 52 | 169-170 | C$_{26}$H$_{32}$N$_2$O (C, H, N) | 1634 | 1.14 (t, 3 H, J = 7.4 Hz), 1.25-2.57 (m, 12 H), 2.57-2.86 (m, 2 H), 3.12 (dd, 2 H, J = 1.6 and 5.8 Hz), 3.80-4.32 (m, 1 H), 4.64-5.13 (m, 1 H), 6.16 (t, 1 H, J = 6.0 Hz), 7.10-7.40 (m, 10 H) |

Example 19

Affinity Towards the Opioidergic Receptors μ, δ, k

The affinity of the compounds synthesized in the preceding examples towards the opioidergic receptors μ, δ, k has been evaluated in vitro by radioreceptorial binding, studies by using the method reported hereinunder.

The technique of the receptorial binding allows to establish if and with what affinity and specificity, a specific compound binds to a particular receptor.

To evaluate the affinity of a specific compound to a particular receptor it is necessary to challenge (in a particular preparation of the tissue wherein those specific receptors are present) the compound to be tested with a radioactive labelled compound with known affinity. The property of the tested compound to displace the radioactive compound gives an index of the affinity of the compound for the binding to that specific receptor. The radioactivity value found in the receptor compound complex allows furthermore to calculate with great precision the amount of compound bound to the receptor. By this method it is therefore possible to quickly identify the affinity of a new compound towards a specific receptor and thus determine its pharmacological activity. By repeating the same experimental design it is possible to evaluate the affinity of the compound towards other kinds of receptors and thus establish its specificity degree.

The receptorial binding technique, besides being used for the screening of new molecules with pharmacological activity, can give useful information on possible changes at the receptorial level, correlated for example with a prolonged exposure to drugs and/or to particular pathologies. In these situations, indeed, changes in the amount of the present receptors, or conformational changes can occur, which alter the affinity of the agonists or antagonists with consequence on the normal function of the receptors themselves.

The experimentation has been carried out according to the guide lines of the European Community for the animal experimentation (EEC n. 86/609), by using laboratory animals (male mices CD1 Charles River Italy, Calco, LC, Italy) lodged twenty in a cage, under standard stabulation conditions (temperature 22±2° C. relative humidity 60%, artificial light with a light/dark cycle of 12 hours). The food and water were at disposal ad libitum.

The binding experiments were carried out according to the following methods.

Receptors k: CD1 male mice weighing 20-25 g were used. The animals were sacrificed by cervical dislocation and the complete brain (excluding the cerebellum) was quickly dissected and kept in ice. The tissue was homogenized in 40 volumes (w/v) of Tris-HCl buffer (50 mM, pH 7.4) by an Ultra-Turrax, then centrifuged for 20 minutes at 48,000×g in a centrifuge kept at 4° C. The resulting supernatant was suspended again in the same buffer and incubated at 37° C. for 30 minutes in a bath kept under oscillation. At the end of the incubation the suspension was centrifuged 48,000×g for 15 minutes and the pellets suspended again in 10 volumes of the Tris-HCl buffer. The binding experiment was carried out in a volume of 1 ml at the temperature of 25° C. with about 800-1000 μg of proteins for sample. The incubation was carried out for 60 minutes in the presence of different concentrations of the ligand $^3$H-U 69.593 (41.7 Ci/mmole). The non specific binding was determined in the presence of U69593 (10 μM). The incubation was stopped by quick filtering by means of a filtration instrument (Brandell®, Gaithersburg, Md., USA) by using GF/C filters (Whatman®).

Receptors μ and δ: the experiments were carried out according to the method described by Unterwald (1995) by using CD1 male mice weighing 20-25 g, lodged 20 for cage under standard stabulation conditions (temperature 22±2° C., relative humidity 60%, artificial light with light dark cycle of 12 hours). After the sacrifice, total brain (excluding the cerebellum) of the animals was quickly removed. The so obtained tissues were quickly homogenized, by Polytron®, in 50 volumes of Tris HCl buffer (50 mM), pH 7.4 and the homogenate then centrifuged at 48,000×g for 20 minutes at 4° C. The resulting pellets were suspended in 50 volumes of the same buffer and the suspension incubated at 37° C. for 45 minutes, in a bath kept under oscillation, so to make easier the separation of the endogenous opioids from the receptors. At the end of the incubation the suspensions were centrifuged at 48,000×g, for 20 minutes at 4° C. and the resulting pellets suspended in 40 volumes of the Tris HCl buffer (50 mM), pH 7.4. The obtained suspension of cerebral membranes was used for the binding tests.

The binding experiment was carried out in a 2 ml volume, at the temperature of 25° C., with 50-100 μg of proteins in each sample; the incubation was carried out for 60 minutes in the presence of 1 nM [$^3$H]-DAMGO (54.5 Ci/mmole) or 1 nM [$^3$H]-DPDPE (45 Ci/mmole), respectively for the study of the receptors μ and δ.

The non specific binding was determined in the presence of naloxone (10 μM). For drawing of the competition curves, at least eight different concentrations of each compound were used. As a reference compound morphine was used at concentrations comprised between $10^{-10}$ and $10^{-5}$ M.

The incubation was interrupted by quick filtration by GF/B filters (Whatman®), by means of a filtration instrument (Brandel®, Gaithersburg, Md., USA). The filters were washed three times with 5 ml of cold Tris HCl buffer (50 mM), pH 7.4.

The radioactivity was determined by a scintillator in liquid phase (Tricarb® 2100, Packard, Meridien, Ill., USA), by using three ml of scintillating fluid (Ultima Gold MV, Packard, Meridien, Ill., USA).

The protein determination was carried out by the Bradford method (1976) by using the protocol and the reactants supplied by Bio-Rad (Milano, Italy).

The affinity of the compounds towards the receptors μ, δ, κ has been expressed in Ki terms.

The results of the binding experiments are shown in Table 2.

TABLE 2

Affinity of the compounds of the invention towards the opioidergic receptors μ, δ and k (affinity values expressed as $K_i$)

| Compound (Example) | $K_i$ μ (nM) | $K_i$ δ (nM) | $K_i$ k (nM) |
|---|---|---|---|
| I-Aa | 5.7 ± 1.0 | 425 ± 25 | 55 ± 25 |
| I-Ab | 7.0 ± 1.5 | 867 ± 44 | 100 ± 5 |
| I-Ac | 56.7 ± 13 | 2000 ± 250 | 2500 ± 125 |
| I-Ad | 10.7 ± 0.3 | 142 ± 25 | 103 ± 7 |
| I-Ba | 8.3 ± 1.2 | 933 ± 33 | 900 ± 100 |
| I-Bb | 4.1 ± 0.35 | 850 ± 58 | 393 ± 23 |
| I-Bc | 68.3 ± 10.9 | >5,000 | >10,000 |
| I-Bd | 20.7 ± 2.33 | 333 ± 5 | 1133 ± 186 |
| I-Ca | 17.0 ± 1.3 | 1667 ± 166 | 410 ± 10 |
| I-Cb | 4.25 ± 0.3 | 1117 ± 216 | 425 ± 38 |
| I-Cc | 3.16 ± 0.6 | 187 ± 29.7 | 40 ± 0.1 |
| I-Da | 40 ± 2.8 | 3875 ± 125 | 1467 ± 317 |
| I-Db | 17.5 ± 1.4 | 3250 ± 166 | 1167 ± 120 |
| I-Dc | 23.3 ± 1.6 | 1688 ± 312 | 1933 ± 233 |

Example 20

Preparation of an Emulsion Containing the Compounds of Formula (I)

0.05 g of the compound of formula I-Ca obtained in Example 17 were dissolved in 1.95 grams of Miglyol® 812S (Sasol). The oily phase was heated to 70° C., 0 and at this temperature it was added dropwise under stirring, (1 drop/second), to an aqueous solution of 1 g of nonionic surfactant Solutol® HS15 (Basf) in 7 ml of distilled water, also maintained at the temperature of 70° C. It is left under stirring of an ultraturrax Politron turboemulsifier (10,000 rpm with a 7 mm sonde) for 15 minutes. 10 g of emulsion are obtained.

The emulsion has been transferred into a 25 ml glass cylinder kept at 400. After one hour the emulsion is warmed to 25° C.

The composition (% by weight) of the emulsion is the following:

| | |
|---|---|
| Miglyol ® 812S (oil): | 19.5% |
| Solutol ® HS15 (surfactant): | 10% |
| Water: | 70% |
| Compound I-Ca: | 0.5% |

The emulsion does not show phase separation at least for five days from the preparation if kept at the temperature of 25° C.

Example 21

Preparation of an Emulsion Containing the Compounds of Formula (I)

0.05 grams of the compound of formula I-Cb (active principle) obtained in Example 17 are solubilized in a mixture of 1.46 g of Miglyol® 812S (Sasol) and 0.48 g of Imwitor® 308 (Sasol). Heating at 70° C. is performed. Then the oily phase is dropwise added under stirring, by using the same device of the preceding example, to a solution of 1 g of nonionic surfactant Solutol® HS15 (Basf) in 7 ml of physiological solution (aqueous phase), maintained at the temperature of 70° C.

At the end the emulsion is cooled at 4° C. and then warmed to the temperature of 25° C. as described in the preceding Example. 10 g of emulsion are obtained.

The composition (% by weight) of the emulsion is the following:

| | |
|---|---|
| Miglyol ® 812S (oil): | 14.6% |
| Imwitor ® 308 (oil): | 4.9% |
| Solutol ® HS15 (surfactant): | 10% |
| Aqueous phase: | 70% |
| Active principle: | 0.5% |

The emulsion does not show phase separation at least for five days from the preparation if kept at the temperature of 2500.

Example 22

Preparation of an Emulsion Containing the Compounds of Formula (I)

0.05 grams of the compound of formula I-Da (active principle) obtained in Example 18 are solubilized in a mixture of 1.45 g of soya oil (pharmaceutical grade) and 0.48 g of Imwitor® 308 (Sasol). Heating at 60° C. is performed. Then the oily phase is dropwise added under stirring, by using the same device of the Example 20, to a solution of 2.5 g of the block copolymer comprising polyoxyethylene and polyoxypropylene chains Lutrol® FF1327 (Basf) in 6 ml of physiological solution (aqueous phase), maintained at the temperature of 60° C.

At the end the emulsion is cooled at 4° C., then warmed to the temperature of 25° C. as described in Example 20. 10 g of emulsion are obtained.

The composition (% by weight) of the components of the emulsion is the following:

| | |
|---|---|
| Soya oil (oil): | 14.5% |
| Lutrol ® F127 | 25% |
| Aqueous phase: | 60% |
| Active principle: | 0.5% |

The emulsion does not show phase separation at least for five days from the preparation if kept at the temperature of 25° C.

Example 23

Preparation of Particles of Polylactate-Polyglycolate Containing the Compounds of formula (I)

10 mg of the compound I-Aa obtained in Example 15 and 100 mg of copolymer PLA-PLGA 50:50, having average molecular weight 40,000-75,000, commercialized mercialized by Sigma Aldrich, have been dissolved in 4 ml of ethyl acetate. The obtained organic solution was emulsified in 8 ml of an aqueous solution at 5% by weight of Solutol® HS15 (Basf) by treating for; 30 minutes with an ultraturrax Politron turboemulsifier (10,000 rpm with 7 mm sonde).

The organic solvent (ethyl acetate) was then removed from the emulsion by heating to 50° C. in a rotating evaporator. An aqueous dispersion of PLA-PLGA particles containing the compound I-Aa is formed. The aqueous dispersion was subjected to three washing cycles by centrifuging with centrifuge test tubes AMICON having membrane with 100,000 MWCO cut off. Each washing cycle was carried out at 4,000 rpm for 20 minutes, adding each time 15 ml of distilled water in the upper section of the test tube, wherein there are the particles.

At the end of the washings the particle aqueous dispersion was lyophilized under the following conditions: temperature −40° C., pressure $5\times10^{-2}$ mbar, time 24 hours.

The obtained particles have been characterized both by transmission electronic microscopy (TEM) and by Photon Correlation Spettroscopy (PCS). The average diameters determined for the particles resulted of 90±20 nm by TEM and 126±5 nm by PCS.

The content of active principle englobed in the particles was determined by solubilizing in dichloromethane a known amount of the obtained sample, then analyzing by UV/Visible spectrophotometer the obtained organic solution. The amount of compound I-Aa determined in the lyophilized sample of nano particles was equal to 70% of that initially solubilized in ethyl acetate.

Example 24

Preparation of Particles of Polylactate-Polyglycolate Containing the Compounds of Formula (I)

The process reported in Example 23 has been repeated, but by using:

compound I-Da obtained in Example 18 instead of compound I-Aa, as organic solvent, dichloromethane in place of ethyl acetate, as surfactant, polyvinyl alcohol instead of Solutol® HS15.

The characterization of the particles obtained after the lyophilization and washing steps as described in the preceding Example has given the following results:

average diameter of 100±20 nm (TEM): 146±15 nm (PCS), the amount of active principle contained in the particles is equal to 67% of that initially solubilized in dichloromethane.

Example 25

Preparation of Lipidic Particles Containing the Compounds of Formula (I)

50 mg of compound I-Ca, obtained in Example 17, were mixed with 1 g of tripalmitine (DYNASAN® 116, Sasol) at the temperature of 70° C. The oily phase was then emulsified, at the same temperature of 70° C., with an aqueous solution of 4 g of Solutol® HS15 in 60 ml of distilled water (60 ml), under stirring by means of Ultraturrax Politron turboemulsifier at 8,000 rpm for 20 minutes. The obtained emulsion was brought to room temperature with formation of a lipid water-based dispersion (tripalmitine) containing compound I-Ca, stabilized by the surfactant Solutol® HS15. The dispersion was then subjected to 4 cycles of treatment in a apparatus Microfluidics 110S (high pressure homogenizer) at the pressure of 120 psi.

The obtained dispersion was characterized by Photon Correlation Spectroscopy (PCS). The average diameters determined for the lipid particles resulted 180±7 nm.

The aqueous dispersion was subjected to three washing cycles by centrifuging with centrifuge test tubes AMICON with membranes 100,000 MWCO cut off. Each washing cycle was carried out at 4,000 rpm for 20 minutes, by adding each time 15 ml of distilled water in the upper section of the test tube, wherein there are the particles.

At the end of the washing process the aqueous dispersion was subjected to lyophilization under the following experimental conditions: temperature −40° C., pressure $5\times10^{-2}$ mbar, time 24 hours.

The content of active principle incorporated in the particles was determined by solubilizing in dichloromethane a known amount of the final sample and analyzing by UV/Visible spectrophotometer the obtained organic solution. The amount of compound I-Ca in the lyophilized sample of nano particles was found equal to 50% of that initially solubilized in tripalmitine.

Example 26

Preparation of Particles of Polyalkylcyanoacrylates Containing the Compounds of Formula (I) Modified with Polyoxyethylene Chains A. Preparation of MePEG (Polyethylenglycol Methylether) Cyanoacetate The esterification reaction of MePEG was carried out under an inert atmosphere (Argon). 2.2696 g of dicyclohexylcarbodiimmide (DCC) and 50 mg of 4-(dimethylamino) pyridine (DMAP), previously dissolved in 5 ml of anhydrous dichloromethane, were added to a solution of cyanoacetic acid (0.9357 g) and of MePEG (11 g) in 25 ml of anhydrous dichloromethane. The obtained sample was stirred for 6 hours at room temperature. The formed solid residue was separated off by filtration under vacuum and washed with dichloromethane (3×20 ml). The filtrate was concentrated under reduced pressure until obtaining a viscous light yellow product. Purification by crystallization with isopropanol was then carried out. After recrystallization 11 g of a beige coloured solid were obtained.

b. Preparation of Hexadecyl Cyanoacetate

The esterification reaction of hexadecanol was carried under an inert atmosphere (Argon). 9.9864 g of dicyclohexylcarbodiimide (DCC) and 50 mg of 4-(dimethylamino) pyridine (DMAP), previously dissolved in 50 ml of anhydrous dichloromethane, were added to a solution of cyanoacetic acid (7.4853 g) and of hexadecanol (10.6674 g) in 50 ml of anhydrous dichloromethane plus 5 ml of ethyl acetate. The obtained sample was stirred for 24 hours at room temperature. Then 50 ml of anhydrous hexane were added. The formed solid residue was separated off by filtration under vacuum, and washed with n-hexane (70 ml). The filtrate was concentrated under reduced pressure until obtaining an amorphous yellow solid. It was afterwards purfied by flash chromatography (oil ligroin/ethyl acetate 9/1). 14 g of a white solid were thus obtained.

c. Copolymerization

The condensation reaction of the two esters was carried out in an Argon atmosphere. 2 ml of formalin 37% weight/volume and 1 ml of dimethylamine 40% weight/volume were added to a solution of hexadecyl cyanoacetate (1.238 g) and MePEG cyanoacetate (2.067 g) in 10 ml of absolute ethanol and 20 ml of anhydrous dichloromethane. The reaction was carried out under magnetic stirring for 25 hours at room temperature. The obtained mixture was concentrated under reduced pressure until obtaining a waxy yellow solid. This was dispersed in water, extracted with dichloromethane, then anhydrified on sodium sulphate and dried under pressure. 3.4 g of poly(MePEG cyano acrylate-co-alkylcyanoacrylate) were thus obtained as a waxy light yellow solid.

d. Preparation of the Particles 30 mg of poly(MePEG cyano acrylate-co-alkylcyanoacrylate) and 5 mg of the compound of formula I-Ca obtained in Example 17 were dissolved in 6 ml of acetone. The organic solution was dropwise added under magnetic stirring to 12 ml of distilled water. The organic solvent was then removed by evaporation, obtaining an aqueous dispersion of nano particles. The particle aqueous dispersion was subjected to lyophilization under the following conditions: temperature $-40°$ C., pressure $5 \times 10^{-2}$ mbar, time 24 hours.

The obtained particles were characterized by both transmission electronic microscopy (TEM) and by Photon Correlation Spectroscopy (PCS). The average particle diameters determined was of 150±17 nm by TEM and 133±10 nm by PCS.

The content of active principle incorporated in the particles was determined by: solubilizing in dichloromethane a known amount of the particle sample and analyzing by UV/Visible spectrophotometry the obtained organic solution. The amount of compound I-Ca determined on the lyophilized sample of nano particles was found to be equal to 600% with respect to that originally solubilized in acetone.

Example 27

Preparation of Lecithin Particles with a Liquid Core

The following components were mixed at 70° C.: 2.65 g of aqueous solution 3% by weight NaCl, 1.1 g of Miglyol® 812S, 1.25 g of a mixture of surfactants made of Solutol® HS15 and Soya Lecithin (Epikuron 200) in a ratio by weight 5:1, 0.005 g of the compound of formula I-Ca obtained in Example 17. The so obtained liquid oily phase, maintained at the temperature of 70° C., was dropwise added (1 drop/second) to 50 ml of distilled water kept at 4° C. and under continuous stirring by using a Ultraturrax Politron® equipment at 7,000 rpm. After the addition of the microemulsion, the dispersion with the formed particles was left under stirring at 4° C. for further 15 minutes. The sample was then sonicated for 1 hour and afterwards filtered on 0.45 micron PTFE filters to remove any residue.

The particles were separated from the aqueous medium with the centrifuge filters "Amicon® Ultra" (cut off 100,000 MWCO), by making four washing cycles (30 minutes, 4,000 rpm, 4° C.). At the end of the washing cycles the particles were dispersed again in water and sonicated for one additional hour. The particle aqueous dispersion was subjected to lyophilization under the following conditions: temperature $-40°$ C., pressure $5 \times 10^2$ mbar, time 24 hours.

The obtained particles were characterized by Photon Correlation Spectroscopy (PCS). The average particle diameter was of 50±7 nm.

The content of active principle incorporated in the particles was determined by solubilizing in dichloromethane a known amount of the final sample and analyzing by UV/Visible spectrophotometer the obtained organic solution. The amount of compound I-Ca determined on the lyophilized sample of nano-particles was found to be equal to 52% with respect to that used in the starting sample.

Example 28

Evaluation of the Analgesic Effect

One of the most important therapeutic indications of the compounds agonist of the opioidergic receptors is pain relief. Morphine is the reference compound of this class of opioidergic derivatives and its use is recommended in cases of acute and chronic pain.

To evaluate the therapeutic properties of the compounds of formula (I) agonist of the opioid receptors in the pain treatment, two animal models, commonly used for the evaluation of the pain threshold in laboratory animals, have been carried out: the Hot Plate test and the Tail Flick test.

a. Hot-Plate

The analgesic effect has been evaluated in accordance with the procedure indicated by Ruiu S. et al. (J. Pharmacol. Exp. Ther. 306(1) (2003) 363-370), by determining the time (latency in seconds) of response to the pain in mice (male CD1, 20-25 g) placed on a plate maintained at the constant temperature of 55±0.2° C.

In the experiment the following behaviours have been considered as pain signs: leg lifting (forelegs or hindlegs), licking of the same, jumping, etc. When one: of said signs was shown by the animal, it was immediately removed from the hot plate, and the relevant latency time registered. To avoid lesions to leg tissues, a maximum latency time (cut-off) of 14 seconds was fixed, after which the animal: was in any case removed from the plate. The values obtained from the experimentation have been expressed as MPE % (maximum possible effect %), according to the formula:

$$MPE = \frac{[\text{Latency Test (sec.)} - \text{Basic latency (sec.)}]}{\text{Cut off (sec.)} - \text{Basic Latency (sec.)}} \times 100$$

wherein latency test is the number of seconds elapsed before the appearance of pain signs in the animal undergoing pharmacological treatment. By basic latency it is meant the seconds elapsed before the appearance of pain signs in the same animal before drug administration.

In particular it has been evaluated the analgesic potency of the compounds of formulae I-Aa (obtained in Example 15), I-Cc (obtained in Example 17) and I-Ba (obtained in Example 16), as the corresponding formates (obtained by treatment of the compounds with formic acid). The carrier was an aqueous solution made of physiological solution, ethanol and Cremophor® EL in the ratios by volume: 18.5:1.0:0.5. The carrier and the formulations containing the compounds of formula (i) or morphine with the carrier, were administered by intraperitoneal route (i.p.) in such volumes to guarantee in the animal dosages of 10 and 20 mg/kg, respectively.

As references the carrier and morphine (10 mg/kg) were used.

For evaluating the duration of the analgesic effect, the % MPE values obtained at different times (15, 30, 60, 120, 240, 360 min.) from the administration of the formulations of the compounds of formula (I) and of the references, have been registered. See Table 3.

b. Tail Flick

For this study, male CD1 mice weighing 20-25 g have been used. The test consists in evaluating the time elapsed between the exposure of a portion of the mouse tail (put at 2 cm from the tail tip) to a small heat source and the moment when the animal removes the tail from the heat source (Ruiu S. et al. in J. Pharmacol. Exp. Ther.; 306(1) (2003) 363-370). This time interval has been automatically calculated by a specific equipment for the Tail-Flick test (Instrument for Tail Flick, Ugo Basile, Italy), equipped with an infrared lamp as a heat source that can be regulated. The equipment automatically records the time during which the mouse tail has remained in contact with the heat source (latency time). To avoid lesions to the tissues, it has been fixed a maximum latency time of 12 sec, after which the mouse tail was in any case removed from the heat source.

As for the Hot-Plate test, the analgesic potency of the compounds of formula I-Aa (obtained in Example 15), I-Cc (obtained in Example 17) and I-Ba (obtained in Example 16) were assayed as their corresponding formates. The carrier was the same as that used in the hot plate test. The carrier and the formulations containing the compounds of formula (I) or morphine and the carrier, were administered by intraperitoneal route (i.p.) at the same doses as in the hot plate test.

As references the carrier and morphine (10 mg/kg) were used.

For evaluating the duration of the analgesic effect, the % MPE values obtained at different times (15, 30, 60, 120, 240, 360 min.) from the administration of the formulations of the compounds of formula (I) and of the references have been registered. See Table 4.

c. Results

The results obtained in the Hot Plate and Tail Flick tests reported respectively in Tables 3 and 4 show that the compounds of formula (I) significantly increase the pain threshold. In fact the MPE % values within 120 minutes from the administration are notably higher than those of the corresponding carrier, and therefore the tested compounds show analgesic properties.

As to said property, it is noted that at 30 minutes from the administration, the analgesic effect of the compounds of formula (I) resulted equal to or even higher than that of the morphine. Besides, with reference in particular to the administered dose: of 20 mg/kg, throughout the tests it has been noticed that the analgesic effect is maintained in time.

TABLE 3

Results of the Hot Plate test
The values in the Table correspond to the ±SEM average of at least 6 animals for each experimental group and observation time-point.

| | MPE % | | | | |
|---|---|---|---|---|---|
| | 30 min | 60 min | 120 min | 240 min | 360 min |
| Carrier | 5 ± 1.5 | −1.7 ± 0.8 | 2.8 ± 1.0 | 1.0 ± 1.2 | −0.5 ± 0.7 |
| Morphine (10 mg/kg) | 39.2 ± 4.1 | 58.5 ± 8.0 | 33.6 ± 4.9 | 21.0 ± 3.3 | 8.5 ± 2.1 |
| Compound I-Aa (10 mg/kg) | 49.5 ± 10.5 | 25.1 ± 6.1 | 6.0 ± 3.0 | 3.2 ± 3.0 | 4.1 ± 1.0 |
| Compound I-Cc (20 mg/kg) | 55.2 ± 10.5 | 40.9 ± 7.8 | 24.1 ± 7.3 | 5.0 ± 4.0 | 0.1 ± 1.1 |
| Compound I-Ba (20 mg/kg) | 68.9 ± 7.2 | 50.5 ± 11.3 | 7.0 ± 2.1 | 6.0 ± 2.1 | −4.0 ± 2.0 |

TABLE 4

Results of the Tail Flick test
The values in the Table correspond to the ±SEM average of least 6 animals for each experimental group and observation time-point.

| | MPE % | | | | |
|---|---|---|---|---|---|
| | 30 min | 60 min | 120 min | 240 min | 360 min |
| Carrier | 2.0 ± 1.5 | −1.0 ± 0.3 | 3.0 ± 1.0 | 0.5 ± 1.1 | −0.8 ± 0.8 |
| Morphine (10 mg/kg) | 60.,2 ± 9.1 | 60.5 ± 6.8 | 39.6 ± 4.0 | 19.1 ± 3.0 | 6.1 ± 1.1 |
| Compound I-Aa (10 mg/kg) | 65.5 ± 6.5 | 20.1 ± 4.1 | 10.0 ± 1.0 | 3.1 ± 2.0 | −3.0 ± 0.5 |

TABLE 4-continued

Results of the Tail Flick test
The values in the Table correspond to the ±SEM average of least 6
animals for each experimental group and observation time-point.

| | MPE % | | | | |
|---|---|---|---|---|---|
| | 30 min | 60 min | 120 min | 240 min | 360 min |
| Compound I-Cc (20 mg/kg) | 80.2 ± 7.5 | 52.9 ± 8.1 | 42.1 ± 8.3 | 14.6 ± 3.0 | 0.0 ± 0.8 |
| Compound I-Ba (20 mg/kg) | 89.9 ± 7.0 | 88.5 ± 10.3 | 9.0 ± 2.5 | 2.0 ± 1.1 | −2.0 ± 1.0 |

The invention claimed is:

1. Nonane and decane diazabicyclic compounds having homopiperazine as main ring, having affinity for the opioidergic μ and/or δ and/or κ receptors and/or for all their receptorial subclasses, with central and/or peripheral activity, having formula (I), the isomeric forms and their mixtures included, wherein one or more ring atoms are optionally in the corresponding isotopic forms:

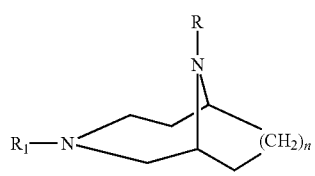

(I)

wherein:
n is an integer equal to 1 or 2;
one of the substituents R and $R_1$ of the nitrogen atoms of the diazabicyclic ring, is a —C(O)—$R_B$ group, wherein $R_B$ is a $C_1$-$C_{10}$ alkyl group, linear or branched when possible,
the other substituent is selected from the following:
(II):

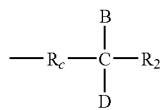

(II)

wherein:
$R_c$ is a bivalent saturated aliphatic chain $C_3$-$C_{10}$, linear or branched when possible,
B is a group selected from the group consisting of: hydrogen, isothiocyanate, CN, OR', C(O)OR', C(O)R', C(O)NR'R", and NR'R", wherein R' and R", equal to or different from each other, are selected from hydrogen, linear or branched when possible $C_1$-$C_7$ alkyl, $C_1$-$C_7$ alkoxy, $C_1$-$C_7$ alkylthio, $C_1$-$C_7$ haloalkyl, $C_1$-$C_7$ haloalkoxy, $C_3$-$C_{15}$ cycloalkyl, aryl or heteroaryl,
D and $R_2$, equal to or different from each other, are selected from:
hydrogen, with the proviso that in formula (II) at least one substituent among B, D and $R_2$ is different from hydrogen;
$C_1$-$C_{10}$ alkyl, linear or branched when possible, optionally substituted,
aryl or heteroaryl, optionally substituted,
$C_3$-$C_{15}$ cycloalkyl, optionally substituted, (III):

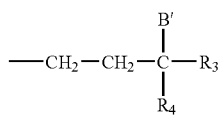

(III)

wherein:
B' is the same as B,
$R_3$ is hydrogen, or an alkyl, aryl, heteroaryl or cycloalkyl substituent as defined for $R_2$,
$R_4$ has the following meanings:
$C_1$-$C_{10}$ alkyl, linear or branched when possible,
$C_3$-$C_{15}$ cycloalkyl, optionally containing one or more heteroaroms,
when B' and $R_3$ are not both hydrogen, $R_4$ has the further meanings of aryl or heteroaryl, (IV):

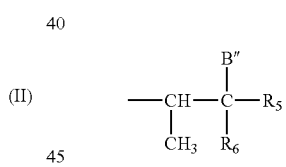

(IV)

wherein:
B" has the same meaning as B',
$R_5$ has the same meaning as $R_3$,
$R_6$ has the same meaning as $R_4$, or is aryl or heteroaryl, (V):

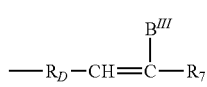

(V)

wherein:
$R_D$ is a bivalent saturated or unsaturated aliphatic chain $C_2$-$C_8$, linear or branched when possible,
$B^{III}$ and $R_7$, equal to or different from each other, have the same meaning of $R_2$, with the proviso that $B^{III}$ and $R_7$ are not both hydrogen;

(VI):

wherein:
$R_E$ is an unsaturated bivalent aliphatic chain $C_2$-$C_8$, linear or branched when possible;
$B^{IV}$ has the same meaning as B;
$D_I$ and $D_{II}$ have the same meaning of $R_2$ as defined above, with the proviso that in formula (VI) at least one substituent among $B^{IV}$, $D_{II}$ and $D_I$ is different from hydrogen;

(VII):

wherein:
$D_{III}$ and $D_{IV}$, equal to or different from each other, have the same meaning of $R_2$ but excluding hydrogen;

(VIII)

 (VIII)

wherein DV has the meanings of $R_4$ as defined above but excluding aryl or heteroaryl;

(IX):

 (IX)

wherein $R_F$ is a saturated or unsaturated bivalent aliphatic chain $C_2$-$C_8$, linear or branched when possible and $R_8$ has the same meaning of $R_2$ as defined above, but excluding the meaning of hydrogen for $R_8$;

(X):

 (X)

wherein $R_9$ has the meaning of $R_4$ as defined above but excluding aryl or heteroaryl.

2. Compounds according to claim 1, wherein B is selected from the group consisting of: OR', C(O)OR', C(O)R', C(O)NR'R", and NR'R", wherein R' and R" are selected from $C_3$-$C_{15}$ cycloalkyl optionally containing one or more heteroatoms, aryl and heteroaryl, wherein each of cycloalkyl, aryl and heteroaryl is optionally substituted with one or more groups selected from hydroxy, halogen, linear or branched when possible $C_1$-$C_{10}$ alkyl.

3. Compounds according to claim 1, wherein D and/or $R_2$ in formula (II) have the meaning of linear or branched when possible $C_1$-$C_{10}$ alkyl, said alkyl optionally substituted with one or more groups, equal to or different from each other, selected from hydroxy, halogen, CN, $C_3$-$C_{15}$ cycloalkyl, aryl, heteroaryl, wherein:
cycloalkyl optionally contains one or more heteroatoms,
$C_3$-$C_{15}$ cycloalkyl, aryl and heteroaryl are optionally substituted with one or more groups selected from hydroxy, halogen, $C_1$-$C_{10}$ alkyl, linear or branched when possible, $C_1$-$C_7$ alkoxy, $C_1$-$C_7$ alkylthio, $C_1$-$C_7$ haloalkyl, $C_1$-$C_7$ haloalkoxy.

4. Compounds according to claim 1, wherein D and/or $R_2$ in formula (II) have the meaning of $C_3$-$C_{15}$ cycloalkyl, optionally containing one or more heteroatoms, wherein D and/or $R_2$ in formula (II) and/or $R_6$ in formula (IV) are aryl, heteroaryl, each of aryl, heteroaryl and cycloalkyl is optionally substituted with one or more of the following, equal to or different from each other, selected from:
linear or branched when possible $C_1$-$C_{10}$ alkyl, optionally substituted with one or more groups, equal to or different from each other, selected from hydroxy, halogen, CN,
$C_3$-$C_{15}$ cycloalkyl optionally containing one or more heteroatoms, cycloalkyl being optionally substituted with one or more groups equal to or different from each other selected from hydroxy, halogen, linear or branched when possible $C_1$-$C_{10}$ alkyl, $C_1$-$C_7$ alkoxy, $C_1$-$C_7$ alkylthio, $C_1$-$C_7$ haloalkyl, $C_1$-$C_7$ haloalkoxy,
arylalkyl or aryl or heteroaryl or heteroarylalkyl optionally substituted with one or more groups, equal to or different from each other, selected from hydroxy, halogen, linear or branched when possible $C_1$-$C_{10}$ alkyl, $C_1$-$C_7$ alkoxy, $C_1$-$C_7$ alkylthio, $C_1$-$C_7$ haloalkyl, $C_1$-$C_7$ haloalkoxy.

5. Compounds according to claim 1, wherein in formula (III) $R_4$ has the meaning of linear or branched when possible $C_1$-$C_{10}$ alkyl, the alkyl being optionally substituted with one or more groups equal to or different from each other selected from hydroxy, halogen, CN, aryl, heteroaryl or $C_3$-$C_{15}$ cycloalkyl optionally containing one or more heteroatoms wherein each of cycloalkyl, aryl or heteroaryl is optionally substituted with one or more groups equal to or different from each other selected from hydroxy, halogen, linear or branched when possible $C_1$-$C_{10}$ alkyl, arylalkyl or aryl or heteroalkyl or heteroarylalkyl, each of arylalkyl or aryl or heteroaryl or heteroarylalkyl being optionally substituted with one or more groups, equal to or different from each other, selected from hydroxy, halogen, linear or branched when possible $C_1$-$C_{10}$ alkyl, $C_1$-$C_7$ alkoxy, $C_1$-$C_7$ alkylthio, $C_1$-$C_7$ haloalkyl, $C_1$-$C_7$ haloalkoxy.

6. Compounds according to claim 1, wherein in formula (III) when $R_4$ has the meaning of $C_3$-$C_{15}$ cycloalkyl optionally containing one or more heteroatoms said cycloalkyl is optionally substituted with one or more of the following groups, equal to or different from each other:
linear or branched when possible $C_1$-$C_{10}$ alkyl, optionally substituted with one or more groups, equal to or different from each other, selected from the following: hydroxy, halogen, CN,
$C_3$-$C_{15}$ cycloalkyl, optionally containing one or more heteroatoms, equal to or different from each other, said cycloalkyl optionally substituted with one or more of the following groups, equal to or different from each other: hydroxy, halogen, $C_1$-$C_{10}$ alkyl, linear or branched when possible, arylalkyl or aryl or heteroaryl or heteroarylalkyl, the arylalkyl or aryl or heteroaryl or heteroarylalkyl groups being optionally substituted with one or more groups, equal to or different from each other, selected from: hydroxy, halogen, linear or branched when possible $C_1$-$C_{10}$ alkyl, $C_1$-$C_7$ alkoxy, $C_1$-$C_7$ alkylthio, $C_1$-$C_7$ haloalkyl, $C_1$-$C_7$ haloalkoxy,
arylalkyl or aryl or heteroaryl or heteroarylalkyl, optionally substituted with one or more groups, equal to or different from each other, selected from hydroxy, halogen, linear or branched when possible $C_1$-$C_{10}$ alkyl, $C_1$-$C_7$ alkoxy, $C_1$-$C_7$ alkylthio, $C_1$-$C_7$ haloalkyl, $C_1$-$C_7$ haloalkoxy.

7. Compounds according to claim 1, wherein in formula (III) B' and $R_3$ are not both hydrogen and $R_4$ has the meaning of aryl or heteroaryl, each of aryl and heteroaryl is optionally substituted with one or more of the following groups, equal to or different from each other:

linear or branched when possible $C_1$-$C_{10}$ alkyl, optionally substituted with one or more groups, equal to or different from each other, selected from the following: hydroxy, halogen, CN, $C_3$-$C_{15}$ cycloalkyl, optionally containing one or more hetroatoms, equal to or different from each other, the cycloalkyl is optionally substituted with one or more of the following groups, equal to or different from each other: hydroxy, halogen, linear or branched when possible $C_1$-$C_{10}$ alkyl, arylalkyl or aryl or heteroaryl or heteroarylalkyl, the arylalkyl or aryl or heteroaryl or heteroarylalkyl groups being optionally substituted with one or more groups, equal to or different from each other, selected from: hydroxy, halogen, linear or branched when possible $C_1$-$C_{10}$ alkyl, $C_1$-$C_7$ alkoxy, $C_1$-$C_7$ alkylthio, $C_1$-$C_7$ haloalkyl, $C_1$-$C_7$ haloalkoxy, arylalkyl or aryl or heteroaryl or heteroarylalkyl, each of these groups optionally substituted with one or more groups, equal to or different from each other, selected from hydroxy, halogen, linear or branched when possible $C_1$-$C_{10}$ alkyl, $C_1$-$C_7$ alkoxy, $C_1$-$C_7$ alkylthio, $C_1$-$C_7$ haloalkyl, $C_1$-$C_7$ haloalkoxy.

8. Compounds according to claim 1, wherein one of R and $R_1$ is a —C(O)—$R_B$ group and the other substituent is selected as follows:

in formula (II) $R_c$ is a bivalent saturated aliphatic chain $C_3$-$C_7$, linear or branched when possible, B is hydrogen, in formula (III) B' is hydrogen, $R_3$ is a substituent selected from alkyl, aryl, heteroaryl or cycloalkyl as defined in $R_2$, wherein $R_4$ comprises also the meaning of aryl or heteroaryl, $R_3$ being different from hydrogen and B equal to hydrogen, in formula (IV) B" is hydrogen, in formula (V) $R_D$ is a saturated or unsaturated bivalent aliphatic chain $C_2$-$C_5$, linear or branched when possible, $B^{III}$ and $R_7$, equal to or different from each other, have the same meaning of $R_2$ with the proviso that $B^{III}$ and $R_7$ are not both hydrogen, in formula (VI) $R_E$ is an unsaturated bivalent aliphatic chain $C_2$-$C_5$, linear or branched when possible, $B^{IV}$ is hydrogen, $D_{II}$ and $D_I$ have the same meaning of $R_2$, with the proviso that in formula (VI) at least one substituent between $D_{II}$ and $D_I$ is different from hydrogen, the formulae (VII), (VIII), (IX) and (X) being as defined above.

9. Compounds according to claim 1, wherein one between R and $R_1$ is a —C(O)—$R_B$ group, $R_B$ being a $C_1$-$C_4$ alkyl group, linear or branched when possible, the other substituent is selected as follows:

in formula (II) $R_c$ is a bivalent saturated aliphatic chain $C_3$-$C_7$, linear or branched when possible, B is hydrogen, in formula (III) B is hydrogen, $R_3$ is a substituent selected from alkyl, aryl, heteroaryl or cycloalkyl as defined for $R_2$, $R_4$ comprises also the meaning of aryl or heteroaryl, in formula (IV) B" is hydrogen, in formula (V) $R_D$ is a saturated or unsaturated bivalent aliphatic chain $C_2$-$C_5$, linear or branched when possible, $B^{III}$ and $R_7$, equal to or different from each other, have the same meaning of $R_2$, with the proviso that $B^{III}$ and $R_7$ are not both hydrogen, in formula (VI) $R_E$ is an unsaturated bivalent aliphatic chain $C_2$-$C_5$, linear or branched when possible, $B^{IV}$ is hydrogen, $D_{II}$ and $D_I$ have the same meaning of $R_2$, with the proviso that in formula (VI) at least one substituent between $D_{II}$ and $D_I$ is different from hydrogen, the formulae from (VII), (VIII), (IX) and (X) being as defined above.

10. Compounds according to claim 1, wherein in formula (I) one of R and $R_1$ is a —C(O)—$R_B$ group, wherein $R_B$ is methyl or ethyl, the other substituent is selected as follows:

In formula (II) $R_c$ is a bivalent saturated alkyl chain $C_3$, linear or branched when possible, B is hydrogen, in formula (III) B' is hydrogen, $R_3$ is a substituent selected from alkyl, aryl, heteroaryl or cycloalkyl as defined for $R_2$, $R_4$ comprises also the meaning of aryl or heteroaryl, in formula (IV) B" is hydrogen, in formula (V) $R_D$ is a saturated or unsaturated bivalent aliphatic chain $C_2$-$C_5$, linear or branched when possible, $B^{III}$ and $R_7$, equal to or different from each other, have the same meaning of $R_2$, with the proviso that $B^{III}$ and $R_7$ are not both hydrogen, in formula (VI) $R_E$ is an unsaturated bivalent aliphatic chain $C_3$, linear or branched when possible, $B^{IV}$ is hydrogen, $D_{II}$ and $D_I$ have the same meaning of $R_2$, with the proviso that in formula (VI) at least one of $D_{II}$ and $D_I$ is different from hydrogen, the formulae (VII), (VIII), (IX) and (X) being as defined above.

11. Compounds according to claim 1, wherein in formula (I) one of R and is —C(O)—$R_B$, wherein $R_E$ is methyl or ethyl, the other substituent is selected from the structures of the following formulae:

formula (III) wherein B' is hydrogen, $R_3$ is a substituent selected from alkyl, aryl, heteroaryl or cycloalkyl as defined in $R_2$, wherein $R_4$ comprises also the meaning of aryl or heteroaryl, formula (VII) wherein $D_{III}$, and $D_{IV}$, equal to or different from each other, have the meaning of $R_2$ but excluding hydrogen, formula (VIII) wherein $D_v$ has the meaning of $R_4$ but excluding aryl or heteroaryl, formula (X) wherein $R_9$ has the meanings of $R_4$ but excluding aryl or heteroaryl.

12. Compounds according to claim 1, having the following formulae:

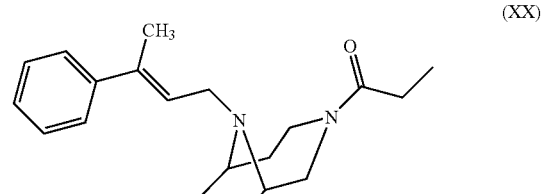

(XX)

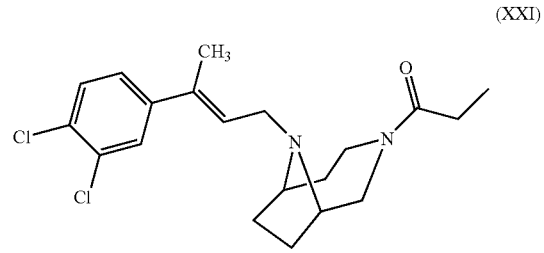

(XXI)

(XXII)
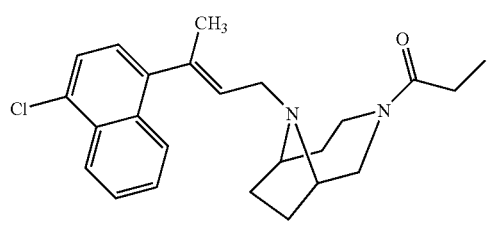
(XXIII)
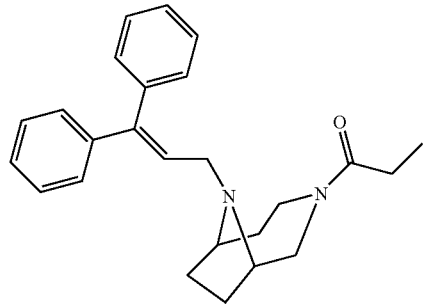
(XXIV)
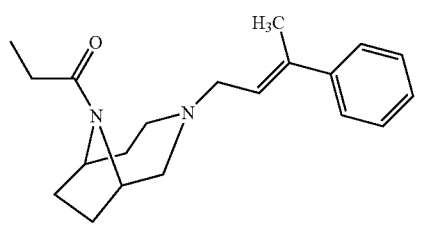
(XXV)
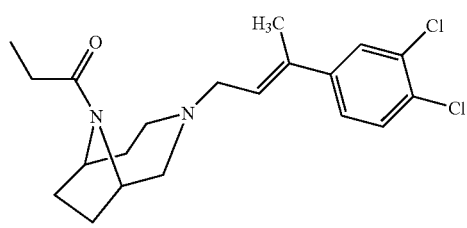
(XXVI)
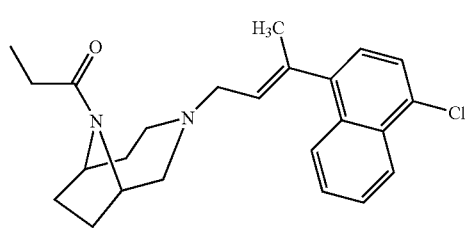
(XXVII)
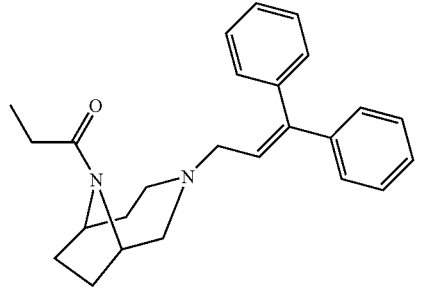
(XVIII)
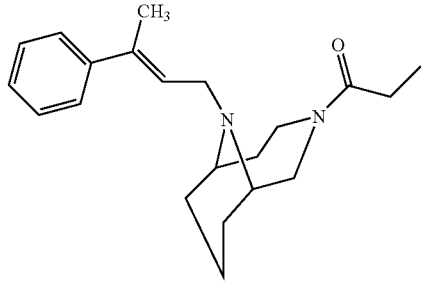
(XXIX)
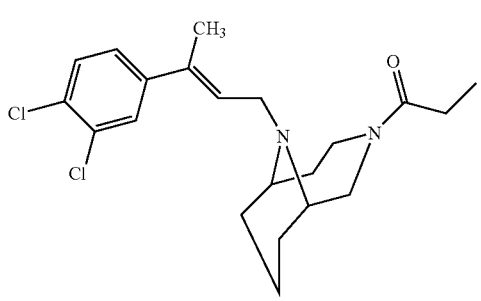
(XXX)
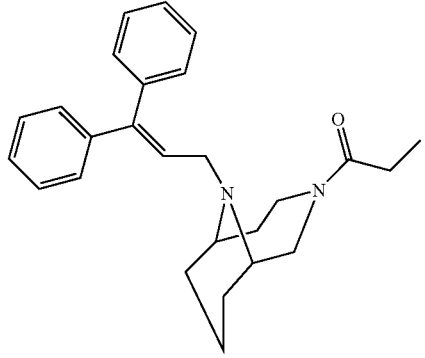
(XXXI)
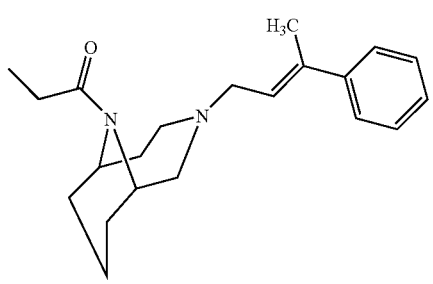
(XXXII)
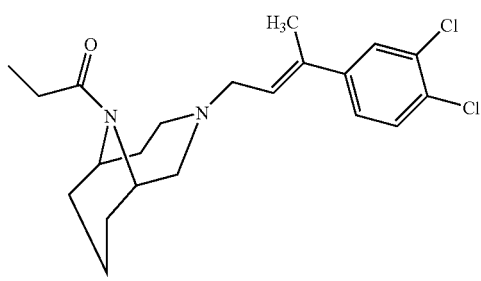

(XXXIII)
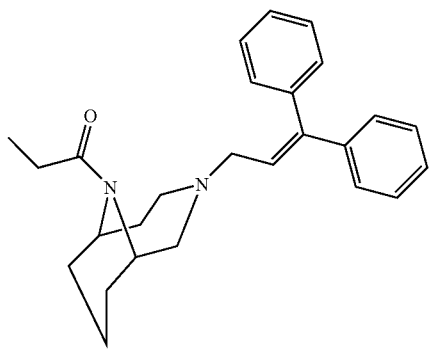
(XXXIV)
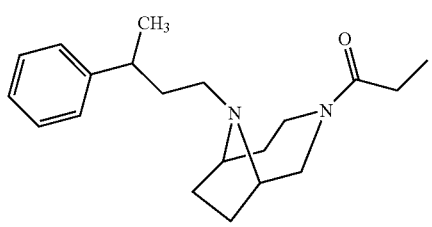
(XXXV)
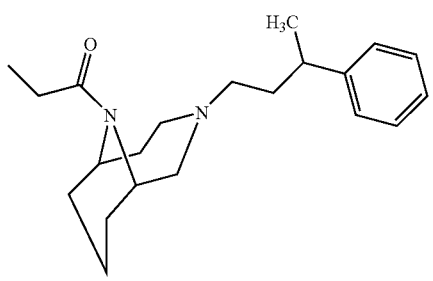
(XXXVI)
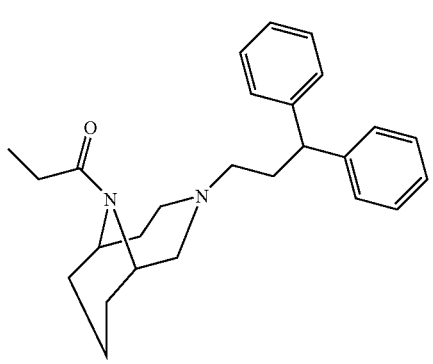
(XXXVII)
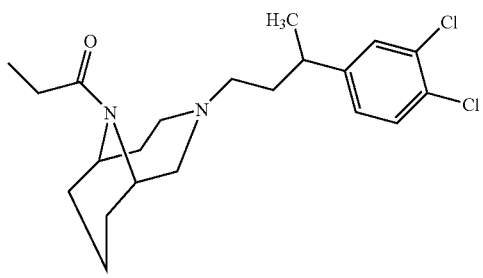
(XXXVIII)
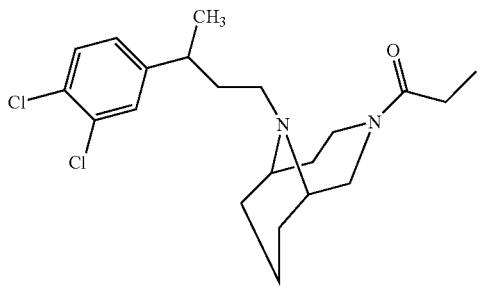
(XXXIX)
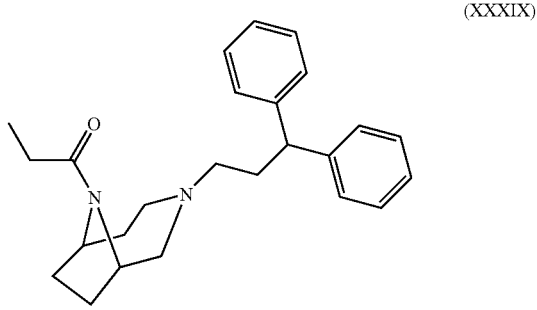
(XXXX)
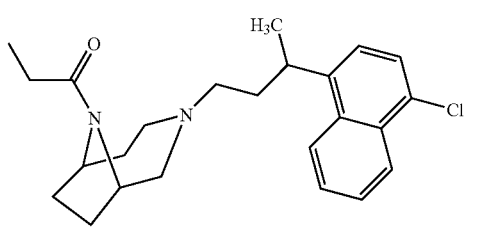
(XXXXI)
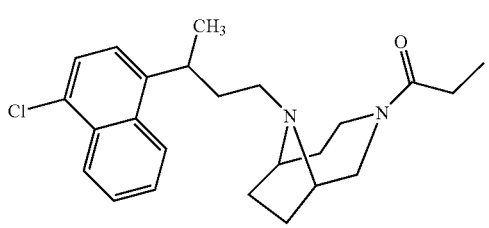
(XXXXII)
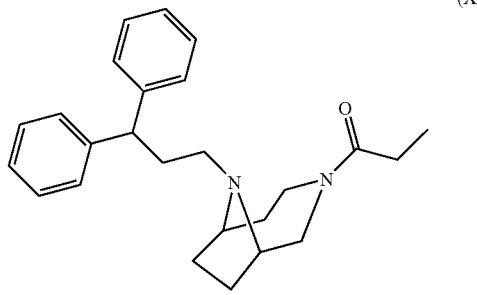

-continued

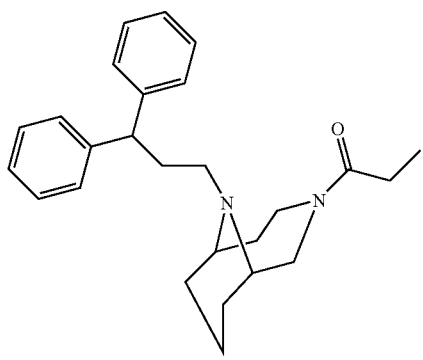

(XXXXIII)

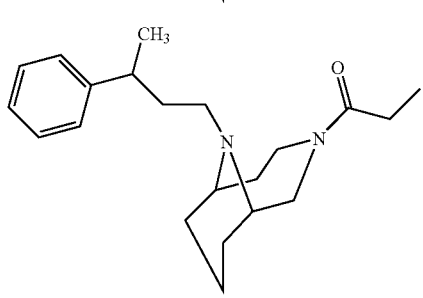

(XXXXIV)

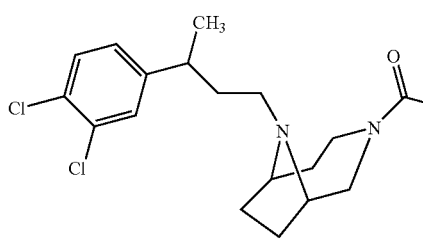

(XXXXV)

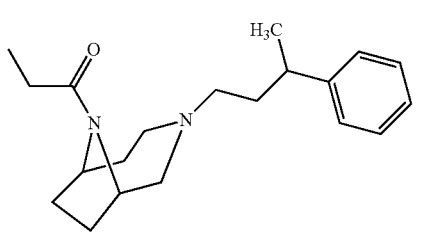

(XXXXVI)

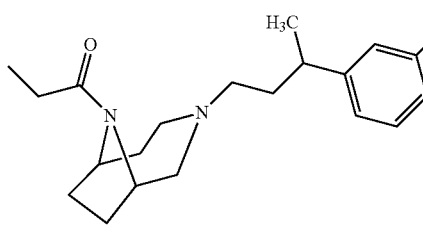

(XXXXVII)

13. Isomers, and respective mixtures, of the compounds according to claim 1.

14. A process for the synthesis of the compounds according to claim 1 comprising the following steps:
- a) reaction of an aldehyde 2 with an amine 1 wherein Rg has the meaning of methyl or benzyl and with the 1,3-acetonedicarboxylic acid 3, to obtain a bicyclic ketone 4,
- b) treatment of the ketone 4 with inorganic acids in the presence of an azide, to obtain an aminolactam 5,
- c) reduction of the aminolactam 5 to obtain the diazabicyclic amine 6,
- d) acylation of the diazabicyclic amine 6 with an alkylated anydride or an acylic chloride, wherein in the anhydride or in the acylic chloride the alkyl chain is $R_B$ as defined above in formula (I), obtaining the amide 7, wherein the acylic substituent —C(O)—$R_B$ has the meaning of $R_1$ in formula (I),
- e) hydrogenation of the amide 7 to obtain an amide 8,
- f) substitution of the hydrogen present on the aminic nitrogen of the amide 8 with the substituent R as defined in formula (I), to obtain the compound 9, as shown in the following:

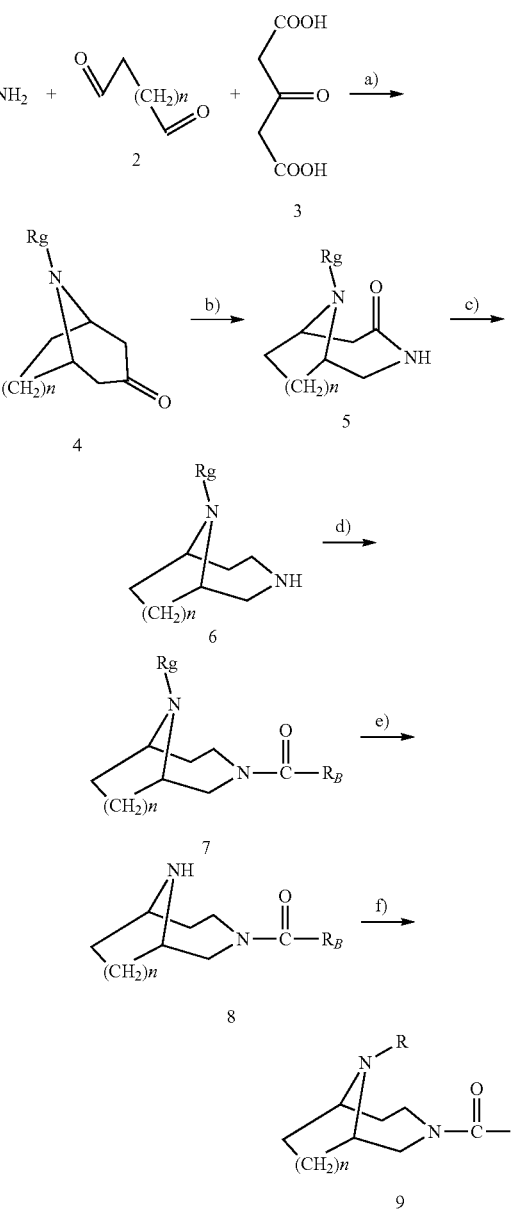

water, said polymers forming organized structures, as aggregates, micelles, liquid crystals and vesicles in the liquid wherein they are solubilized.

15. A process according to claim 14, wherein the compound 8, alternatively to step f), is reacted according the following steps f') and g'):
- f') thermal rearrangement of amide 8 and obtainment of the diazabicyclic compounds 8a, wherein the acylic substituent —C(O)—$R_B$ of the amidic nitrogen has the meaning of R in formula (I), g') substitution of the hydrogen present on the aminic nitrogen of the compound 8a with the substituent $R_1$ as defined in formula (I), and obtainment of the compound 9a,

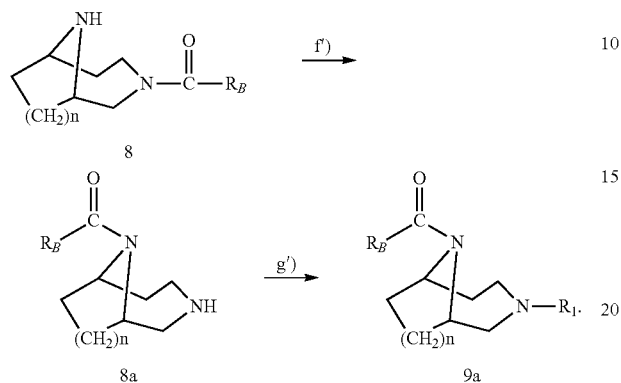

16. A process according to claim 14 wherein, alternatively to steps d)-f), the following steps from g) to k) are used:

g) protection of the nitrogen atom in position 3 of the diazabicyclic amine 6, obtaining compound 10, h) hydrogenation of compound 10 to obtain the diazabicyclic aminocarbamate compound 11, i) acylation of the diazabicyclic amine 11 with an alkyl anhydride, or an acyl chloride, wherein in both compounds the alkyl chain is $R_B$ as defined in formula (I) to obtain the amide 12, wherein the acyl substituent —C(O)—$R_B$ of the amidic nitrogen has the meaning of R in formula (I), j) deprotection of the aminic group, obtaining compound 8a, k) substitution of the hydrogen present on the aminic nitrogen of the compound 8a with the substituent $R_1$ as defined in formula (I), and obtainment of the compound 9a,

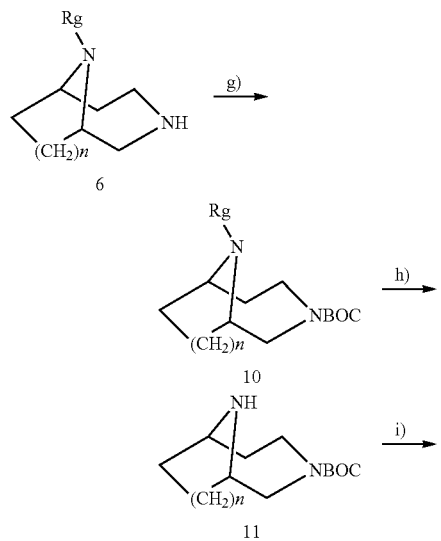

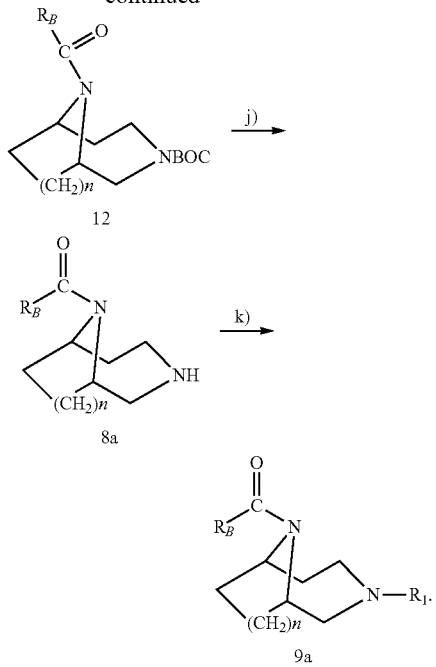

17. Pharmaceutical compositions comprising the compounds according to claim 1 and pharmaceutically acceptable excipients.

18. Pharmaceutical compositions according to claim 17 comprising, as % by weight,
compounds 0.5-20%
surfactants, 0.05-0.5%
disgregating agents 2.5-10%.

19. Pharmaceutical compositions according to claim 17 comprising the compounds and hydroxypropyl methyl cellulose.

20. Pharmaceutical compositions according to claim 19, wherein hydroxypropyl methyl cellulose is present in the core of the capsules or tablets, and/or in the tablet coating.

21. Pharmaceutical compositions according to claim 17 under the form of oil in water emulsions, wherein the compounds, or solubilized in an organic phase, are dispersed in an aqueous phase by using one or more amphiphilic compounds.

22. Pharmaceutical compounds according to claim 21, wherein the amphiphilic compounds are selected from surfactants and/or polymers soluble in oil or in 23. Formulations according to claim 21 having the following composition (% by weight):

| | |
|---|---|
| compounds | from 0.005 to 20% |
| one or more oils | from 0 to 50% |
| one or more amphiphilic compounds | from 0.01 to 50% |
| additives | from 0 to 50% | the complement to 100% being water or a saline aqueous solution, optionally buffered.

24. Pharmaceutical compositions according to claim 17 comprising the compounds and micro- and/or nano-particles of lipids or pharmaceutically acceptable polymers, said compounds being incorporated inside and/or on the surface of said particles.

25. Pharmaceutical compositions according to claim 24, wherein the lipidic particles are selected from those based on fatty acids or their esters having a melting point higher than 40° C., or mixtures between fatty acids or esters of fatty acids with melting point higher than 40° C. and oils liquid at room temperature, or they are formed of a surface layer of soya bean lecithin enclosing a liquid lipidic core.

26. Pharmaceutical compositions according to claim 24, wherein the polymers are natural or synthetic.

27. Pharmaceutical compositions according to claim 26, wherein the natural polymers are proteins and polysaccharides.

28. Pharmaceutical compositions according to claim 26, wherein the synthetic polymers are selected from polyorganophosphazenes, polyanhydrides, polyamides, polyorthoesters, polyalkylcyanoacrylates and polyesters.

29. Pharmaceutical compositions according to claim 28, wherein the polymers are selected from polyalkylcyanoacrylates, polylactate polyesters and polylactate/polyglycolate copolymers.

30. Pharmaceutical compositions according to claim 24, wherein the particles are modified on their surface both by chemico-physical adsorption of one or more surface modifiers and by chemical functionalization.

31. Pharmaceutical compositions according to claim 30, wherein the surface modifiers are selected from compounds comprising polyoxyethylene or peghilated chains, proteins, antibodies and compounds which are recognized by specific receptors expressed at the level of physiological barriers.

32. Pharmaceutical compositions according to claim 31, wherein the particle surface modifiers are directly linked to the main structure of the polymer or are covalently linked to the polymer by linkers having main structure comprising saturated or unsaturated alkyl chains, linear or branched, and/or aromatic and/or polyoxyethylene chains.

33. Pharmaceutical compositions according to claim 32, wherein the linker is formed of polyoxyethylene chains or PEG.

34. A method for identifying and marking the opioidergic receptors $\mu$ and/or $\delta$ and/or $\kappa$ and/or their receptorial subclasses in mammals and in an individual comprising administering to mammals or to an individual the compounds of claim 1 comprising radioactive isotopes.

35. A method for therapeutic treatment of diseases and disorders, comprising administering to an individual in need thereof an effective amount of the composition according to claim 17, wherein the diseases and disorders are selected from the group consisting of: pain, post surgery pain, chronic pain, neuropathic pain, alcoholism, constipation, diarrhea and other disorders of the gastrointestinal tract, nausea, vomit, dermatitis, obesity and other disorders connected with appetite, depression, smoke dependence, sexual dysfunctions, shocks, cerebral trauma, spinal damages, and eye pathologies selected from glaucoma and intraocular hypertension.

* * * * *